(12) United States Patent
Haak

(10) Patent No.: US 8,827,960 B2
(45) Date of Patent: Sep. 9, 2014

(54) CATHETER ANCHORING SYSTEM, APPARATUS AND METHOD

(75) Inventor: Jason D. Haak, Sioux Falls, SD (US)

(73) Assignee: A & R Possibilities, LLP, Sioux Falls, SD (US)

( * ) Notice: Subject to any disclaimer, the term of this patent is extended or adjusted under 35 U.S.C. 154(b) by 453 days.

(21) Appl. No.: 13/029,944

(22) Filed: Feb. 17, 2011

(65) Prior Publication Data

US 2012/0041377 A1   Feb. 16, 2012

Related U.S. Application Data

(63) Continuation-in-part of application No. 12/855,552, filed on Aug. 12, 2010, now Pat. No. 8,425,467, and a continuation-in-part of application No. 12/102,139, filed on Apr. 14, 2008, now abandoned.

(60) Provisional application No. 61/390,489, filed on Oct. 6, 2010.

(51) Int. Cl.
*A61M 5/32* (2006.01)
*A61M 25/02* (2006.01)
*D04H 3/011* (2012.01)

(52) U.S. Cl.
CPC ....... *D04H 3/011* (2013.01); *A61M 2025/0247* (2013.01); *A61M 25/02* (2013.01); *A61M 2025/028* (2013.01); *A61M 2025/0266* (2013.01)
USPC .......................................................... 604/174

(58) Field of Classification Search
CPC ................... A61M 25/02; A61M 2025/0266; A61M 2025/0293
USPC .................................................. 604/174–180
See application file for complete search history.

(56) References Cited

U.S. PATENT DOCUMENTS

| 3,826,254 | A |   | 7/1974  | Mellor |
|---|---|---|---|---|
| 3,834,380 | A |   | 9/1974  | Boyd |
| 4,165,748 | A |   | 8/1979  | Johnson |
| 4,857,058 | A | * | 8/1989  | Payton .......................... 604/180 |
| 5,702,371 | A |   | 12/1997 | Bierman |
| 5,833,665 | A |   | 11/1998 | Bootman et al. |
| 6,224,571 | B1 |   | 5/2001 | Bierman |
| 6,428,515 | B1 | * | 8/2002 | Bierman et al. ............... 604/174 |
| 7,648,492 | B2 | * | 1/2010 | Bierman ....................... 604/513 |
| 2003/0229313 | A1 |   | 12/2003 | Bierman |
| 2008/0039798 | A1 | * | 2/2008 | Bierman ....................... 604/174 |

* cited by examiner

*Primary Examiner* — Nicholas Lucchesi
*Assistant Examiner* — Melissa A Snyder
(74) *Attorney, Agent, or Firm* — Jeffrey A. Proehl; Woods, Fuller, Shultz & Smith, P.C.

(57) ABSTRACT

A catheter anchoring system, apparatus and method for securing a catheter to a patient's skin, having two flexible side members and a cross-member therebetween to which a retaining assembly is mounted. The retaining assembly may hold a catheter hub at an angle for patient comfort. Gripping tabs secure to each retaining assembly side are gripped while advancing a cannula guide needle into the patient's vein and while attaching the catheter hub to a medical accessory, such as intravenous (I.V.) tubing, for increased patient comfort, reduction of the risk in contamination and patient infection, and to more easily and quickly start an I.V.

22 Claims, 28 Drawing Sheets

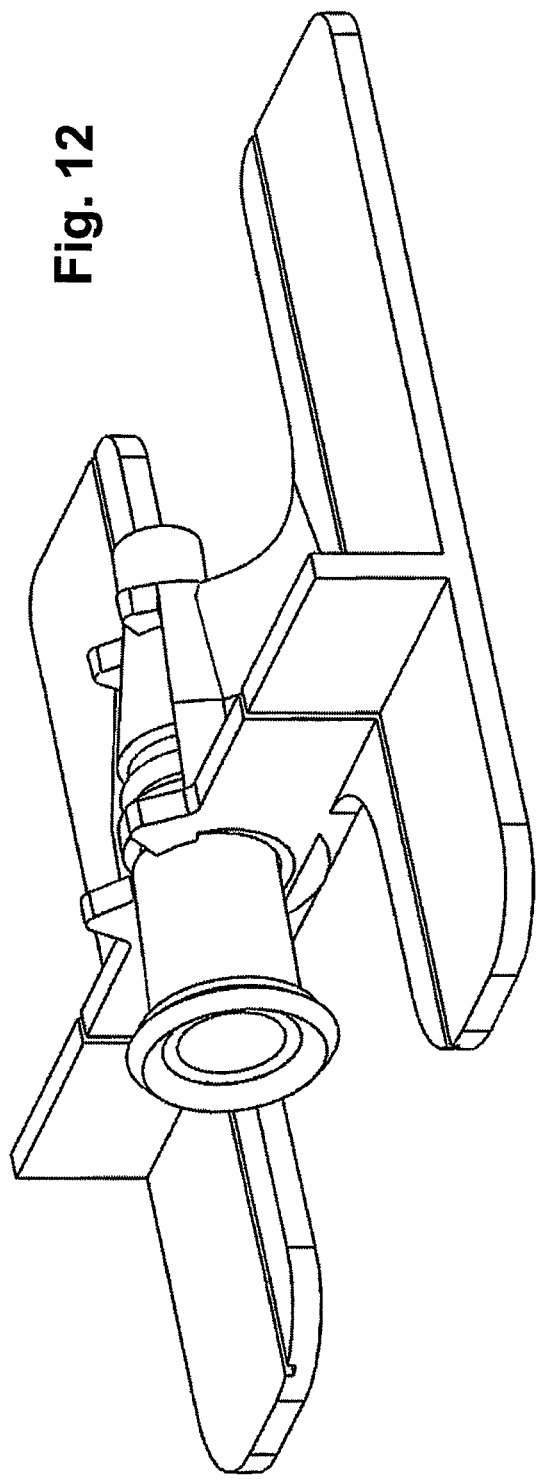

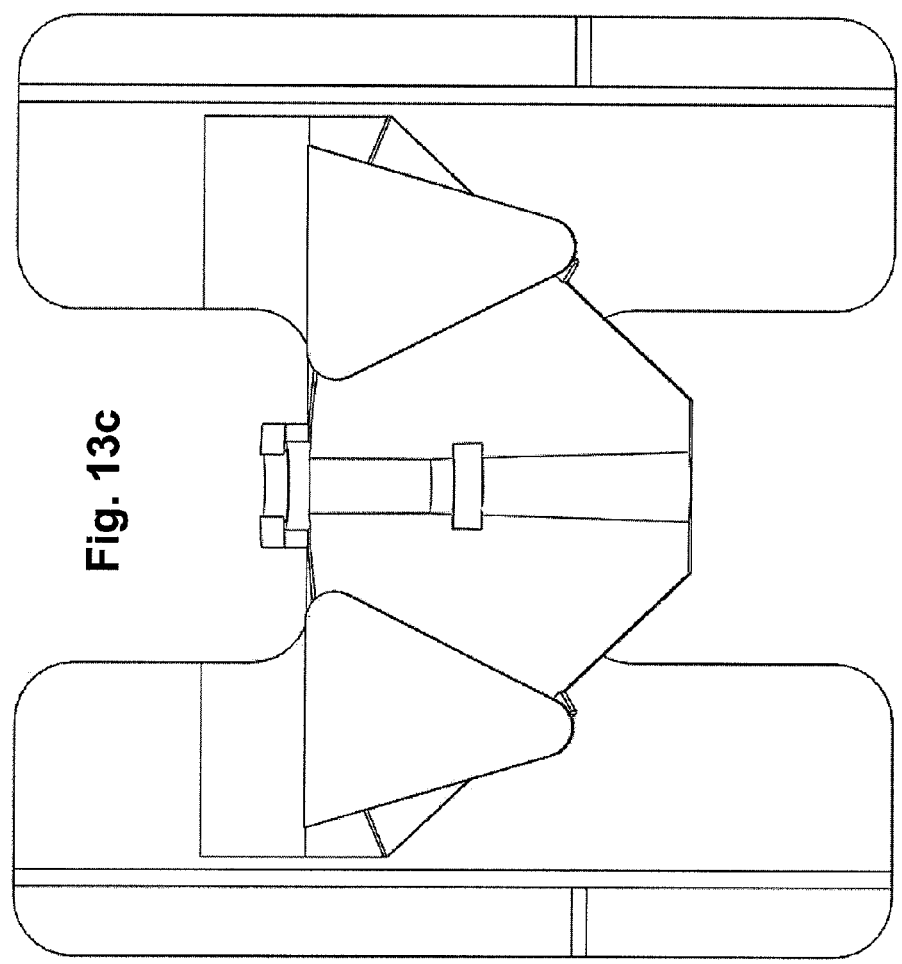

CATHETER ANCHORING SYSTEM, APPARATUS AND METHOD

CROSS-REFERENCE TO RELATED APPLICATIONS

The present application is a continuation in part of U.S. application Ser. No. 12/855,552 entitled "CATHETER TUBE ANCHORING DEVICE" which was filed Aug. 12, 2010, and is incorporated by reference and which was a continuation in part of U.S. application Ser. No. 12/102,139 entitled "CATHETER TUBE ANCHORING DEVICE" which was filed on Apr. 14, 2008. The present application additionally claims the priority of U.S. Provisional Application Ser. No. 61/390,489 entitled "CATHETER ANCHORING SYSTEM, APPARATUS AND METHOD" which was filed Oct. 6, 2010, and is incorporated by reference.

TECHNICAL FIELD

The subject disclosure relates to catheter anchoring and supporting devices, and more specifically relates to catheter anchoring system, apparatus and method characterized by a removably mountable anchoring device for receiving a catheter hub of a catheter assembly, such that the anchoring device may be used as a guide to insert a cannula guide needle and associated cannula (e.g., intravenous cannula) of a catheter assembly into a patient's vein. Mounting the anchoring device to the patient limits movement of the catheter assembly in relation to the patient after cannula insertion. The anchoring device may dispose the catheter cannula at a preferred angle in relation to the patient. The anchoring device is shaped to facilitate asepsis when wrapped with an aseptic dressing. The subject disclosure is particularly relevant to aiding in the insertion of an intravenous (I.V.) cannula, increasing patient comfort and safety, reducing the risk of I.V. site contamination, and reducing the risk of patient infection.

BACKGROUND

A variety of catheter anchoring and supporting devices are discussed in the prior art. One example is a catheter anchoring and supporting device which has two adhesive members connected by an adhesive bridge to secure the members in a doubled over form when the two main members are used to position a catheter tube to a patient. Another example is catheter anchoring and supporting system that has an adhesively-attachable single-piece having two channels connected by a bridge, each channel for receiving a tubular segment.

However, these catheter anchoring and supporting system and devices do not address the desirable feature of aiding in the insertion of a catheter cannula into a catheter insertion site (e.g., a vein) of a patient. These catheter anchoring and support systems do not receive the hub of a catheter. Further, these catheter tube holders do not provide adequate adhesion between the patient's skin and the catheter insertion site to prevent a substantial displacement of the inserted cannula from the insertion site such as when any outward force is applied to the catheter tubing when moving a patient or when a patient is moving the area having the cannula inserted therein.

What is needed is an adhesively-attachable catheter anchoring apparatus having two side members and a cross-member therebetween, the cross-member having a retaining assembly integrated therein for receiving the catheter hub of a catheter assembly and for holding the associated cannula guide needle and the surrounding cannula at approximately a 3-degree angle (e.g., or any desired angle) and further having two vertically-oriented gripping tabs disposed on each side of the retaining assembly, to optionally be gripped while advancing the catheter assembly in the direction to pierce the vein with the cannula guide needle and to guide the cannula into a desired vein without requiring operator contact with the cannula or cannula guide needle, thus reducing the risk of an operator contaminating the catheter, thereby reducing the risk of patient infection, while also making starting the I.V. easier and faster. The present catheter anchoring apparatus addresses the foregoing needs by providing an adhesively-attachable H-shaped catheter anchoring apparatus with two side members and a cross-member there between, the cross-member having a retaining assembly integrated therein for receiving a catheter hub in a position desirable for insertion and for assisting in the advancement of a cannula guide needle into a patient's vein.

SUMMARY

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of this summary is to present some concepts related to some exemplary non-limiting embodiments in a simplified form as a prelude to the more detailed description of the various embodiments that follow.

An embodiment of the present catheter anchoring system, apparatus and method includes a rectangular first side member having an upper portion, a lower portion, an inner side, and an outer side. A rectangular second side member is in a closely-spaced, parallel relation to the rectangular first side member. The second side member has a top portion, a bottom portion, an inner edge and an outer edge. A cross-member is located between the first side member and the second side member, such that the apparatus attains an H-shaped configuration. The cross-member is substantially rectangular having a top side, a bottom side, an outer first edge, an outer second edge, a front edge, and a rear edge. A retaining assembly is located on the cross-member with a longitudinally positioned channel inside for removably securing a catheter hub. When the apparatus is placed on a patient's arm, the retaining assembly has a right side and a left side. The retaining assembly is mounted to the center of the top side of the cross-member. A plurality of retaining fingers is mounted to the right side and the left side of a retaining assembly. A first gripping tab is mounted to the top side of the cross-member in vertical relation to it and between the retaining assembly right side and the outer first edge of the cross-member. A second gripping tab is mounted to the top side of the cross-member in vertical orientation to the top side and between the retaining assembly left side and the outer second edge of the cross-member. A vertical tab is mounted to the top side of the cross-member. The first side member and the second side member are in vertical orientation thereto and between the outer side of the first side member and the outer edge of the second side member. The vertical tab has a front face, a rear face, and a bottom edge surface. The bottom edge surface is connected to the top side of the cross-member. The first side member and the second side member are in parallel relation to the front edge. Adhesive for an adhesive layer is bonded to a bottom surface of the apparatus. The adhesive is selected from a class of adhesives that are suitable for use on human skin. A backing removably covers the adhesive layer. According to an embodiment, the backing has additional, continuous backing that is substantially the same size as the size of backing that removably cover the adhesive layer. The additional backing is folded over the backing. The additional backing extends to the side of the catheter apparatus opposite the fold. A backing removal extension piece, that is attached to the backing, extends beyond the catheter apparatus for removal of the backing through the act of pulling the backing removal extension piece, the attached additional backing, and exposing the attached backing.

Another embodiment of the present catheter anchoring system, apparatus and method is provided to securely anchor a catheter to a site on a patient's skin. The device has a flexible, rectangular first side member with an upper portion, a lower portion, an inner side, and an outer side and a flexible, rectangular second side member with a top portion, a bottom portion, an inner edge, and an outer edge. The side members are adapted to be secured to the skin of a patient in closely-spaced, parallel relation. The device further features a rigid cross-member having top side, a bottom side, an outer first edge, an outer second edge, a front edge, and a rear edge. The outer first edge is affixed to the center of the upper portion, near the inner side of the first side member and the second edge affixed to the center of the top portion, near the inner edge of the second side member. A retaining assembly has a longitudinally disposed channel therein for removably securing a catheter adaptor. The retaining assembly is mounted to the center of the top side of the cross-member. An indention in the rear edge of the cross-member is adjacent to the retaining assembly. The indention is configured to allow a catheter hub to be removably secured within the channel. A first gripping tab is mounted to the top side of the cross-member in a vertical relation thereto and between the retaining assembly right side and the first edge of the cross-member. The first gripping tab has a front side, a rear side, and a bottom edge. The bottom edge is affixed to the top side of the cross-member in a parallel position in relation to the front edge. A second gripping tab is mounted to the top side of the cross-member in vertical relation thereto and between the retaining assembly left side and the second edge of the cross-member. The second gripping tab has a front wall, a rear wall and a lower edge. The lower edge is affixed to the top side of the cross-member in a parallel position in relation to the front edge. An adhesive layer is located on the lower portion of the first side member, on the bottom portion of the second side member, and on the cross-member. A backing removably covers the adhesive layer. The backing includes a backing removal extension piece.

To use the present device, before insertion of the catheter, the hub of the catheter is snapped into the retaining assembly by the user, such as a nurse or physician. Then, gripping one of the tabs on either side of the retaining assembly, depending on the dominant hand of the user, the catheter is advanced after locating and piercing the vein with a cannula guide needle. Using the tabs to advance the catheter reduces the risk of an operator contaminating the catheter and passing bacteria to the patient because the operator's gloved fingers would not come into direct contact with the catheter itself or the cannula. Conventionally, a user uses a thumbnail to push on a ridge of the hub of the catheter thereby making it very easy to contaminate the catheter by touching the catheter (e.g., cannula) before it enters the vein, which may occur even more often when the catheter operator has large fingers. After the catheter is in place, the operator holds one of the tabs while attaching, for example, a saline lock or I.V. tubing with the other hand. The side members and cross-member are then slightly lifted as the backing is removed, and then the entire apparatus is pressed down to secure the device to a patient's skin. This device is much less cumbersome than securing a catheter into place with tape, particularly when the nurse or physician is wearing gloves. In addition, the present device reduces a patient's pain when moving about because the catheter and I.V. do not pull at the site of the insertion.

As such, the general purpose of the improved catheter anchoring system, apparatus and method which has all of the advantages of the prior art mentioned heretofore and many novel features that result in an improved catheter anchoring system, apparatus and method which is not anticipated, rendered obvious, suggested, or even implied by the prior art, either alone or in combination thereof.

An object of the present catheter tube anchoring device to reduce the risk of contamination of a catheter through contact with non-sterile surfaces, thereby reducing the risk of patient infection.

Another object of the present catheter tube anchoring device is to make the starting of an I.V. much easier and faster than permitted by prior art devices.

Yet another object of the present catheter tube anchoring device is to easily secure a catheter to a patient's skin.

Still further, another object of the present catheter tube anchoring device is to substantially immobilize the IV to the skin of a patient, thereby reducing pain caused by movement of the IV in relation to the patient.

Thus has been broadly outlined the more important features of the improved catheter tube anchoring device so that the detailed description thereof that follows may be better understood and in order that the present contribution to the art may be better appreciated.

The above-described deficiencies of today's systems for catheter anchoring are merely intended to provide an overview of some of the problems of conventional systems, and are not intended to be exhaustive. Other problems with the state of the art and corresponding benefits of some of the various non-limiting embodiments may become further apparent upon review of the following detailed description.

BRIEF DESCRIPTION OF THE DRAWINGS

Various non-limiting embodiments are further described with reference to the accompanying drawings in which:

FIG. 12 is a schematic perspective rear view of an embodiment having a catheter hub inserted therein.

FIG. 13c is a schematic top view of an embodiment containing a winged catheter hub attachment.

DETAILED DESCRIPTION

Overview

Figure 1:
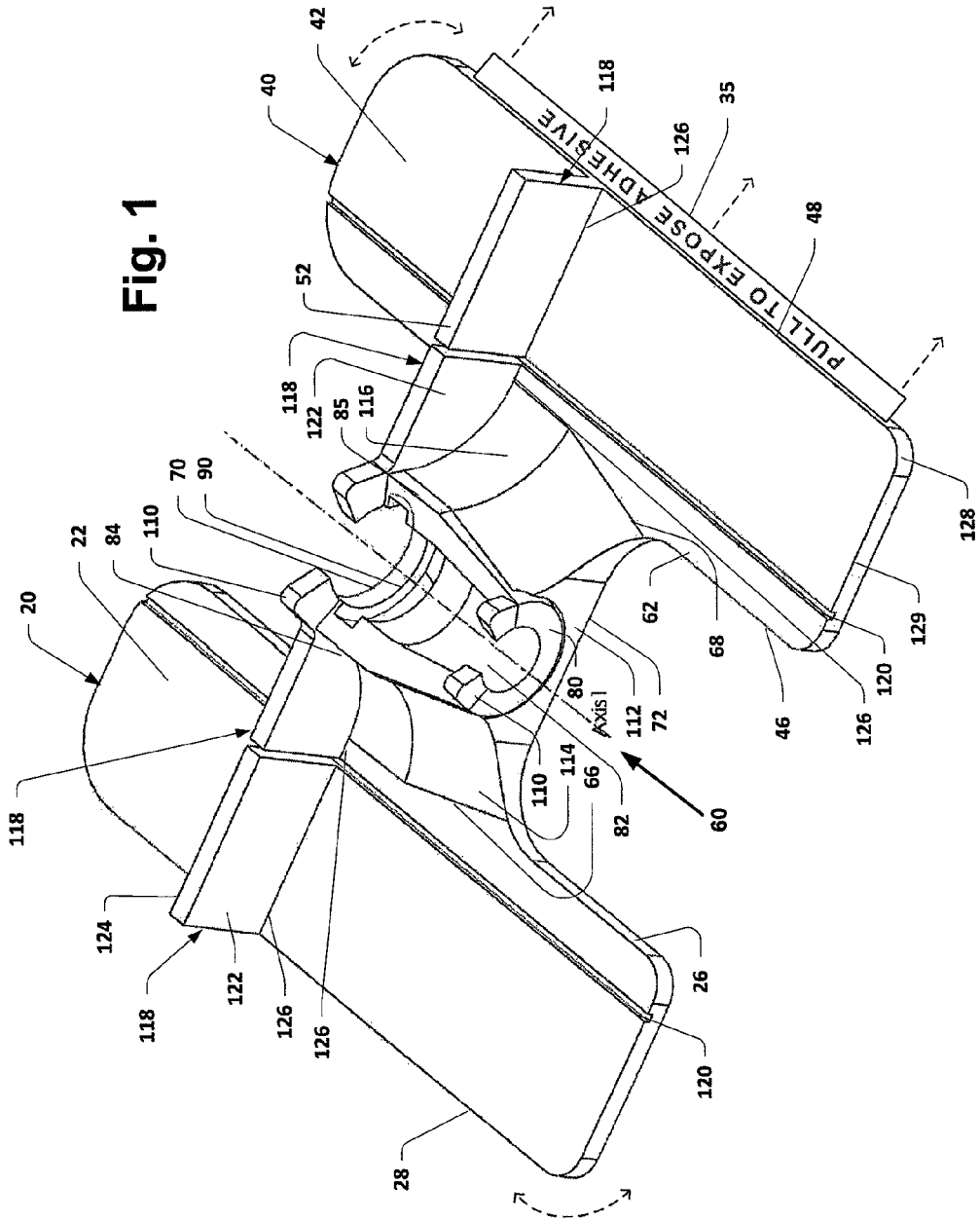
FIG. 1 is a schematic isometric top view of an embodiment of the catheter anchoring system, apparatus and method, according to an embodiment.
Figure 2:
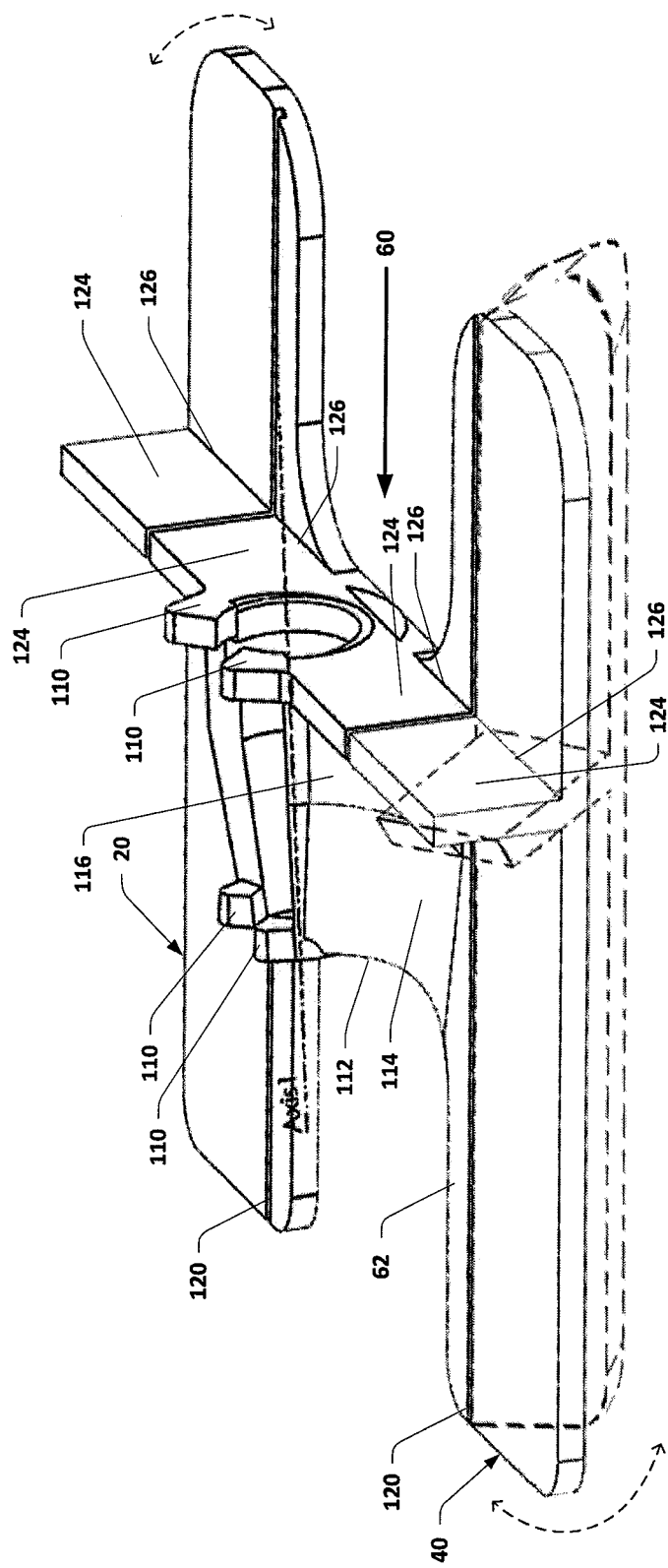
FIG. 2 is a schematic perspective right side view of an embodiment of the present disclosure.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, well-known structures and devices may be shown in block diagram form in order to facilitate describing the claimed subject matter.

Moreover, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or." Therefore, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

With reference now to the drawings, and in particular FIGS. 1 through 31 thereof, various embodiments employing the principles and concepts of the present catheter anchoring system, apparatus and method, generally designated by the reference number 10, will be described.

Referring to FIGS. 1 through 31, various embodiments of the present catheter anchoring system, apparatus and method 10 are used to secure a catheter assembly (e.g., including a cannula placed in the skin and a medical attachment such as intravenous tubing connected to a hub in fluid communication with said cannula) to a patient. The present apparatus 10 provides a rectangular first side member 20, a rectangular second side member 40 in closely-spaced, parallel relation to the first side member 20, and a cross-member 60 there between thereby forming an H-shaped configuration, according to some embodiments. It is recognized by those skilled in the art that the cross-member 60 may be placed at any location along the parallel side members according to some embodiments. The first side member 20 has an upper portion 22, a lower portion 24, inner side 26, and an outer side 28. The second side member 40 has a top portion 42, a bottom portion 44, an inner edge 46, and an outer edge 48.

According to an embodiment shown in FIGS. 25 through 31, the generally rectangular cross-member 60 has top side 62, a bottom side 64, an outer first edge 66, an outer second edge 68, a front edge 70, and a rear edge 72. The outer first edge 66 is attached to the inner side 26 of the first side member 20. The outer second edge 68 is attached to the inner edge 46 of the second side member 40. According to an embodiment, the outer first edge 66 is attached at any point along the inner side 26 of the first side member 20, such that the cross-member 60 and the outer first edge 66 are in a substantially perpendicular configuration. The outer second edge 68 is attached at any point along the inner edge 46 of the second side member 40, such that the cross-member 60 and the outer second edge 68 are in a substantially perpendicular configuration.

According to an embodiment as shown in FIGS. 1 through 31, the present apparatus is constructed from a single polymer having operational elastomeric characteristics such that the apparatus is selectively flexible according to the type of polymer chosen. One application of a flexible apparatus is that a single design (e.g., an apparatus configuration of a single size) of the apparatus can adapt to (e.g., fit) a greater percentage of patients' arms (e.g., appendages). Another application of a flexible apparatus is to increase usability in situations where a patient's skin may be very tender and sensitive to the placement of rigid or ill-fitting medical devices on their body. A substantial benefit is realized by having the ability to change the composition of the polymer used as the substrate for the apparatus and as a result, directly change the operational elastomeric characteristics of the apparatus as a whole. As might be expected, the possible applications of this ability are numerous. According to some embodiments, the use of more than one polymer is contemplated, for example, for creating a soft surface to be placed against a patient's skin and a rigid surface to receive the catheter hub. Other such combinations of more than one polymer are possible for a variety of purposes, but are not illustrated here.

Corners 128 (e.g., where edges of two side members meet) of the first and second side members, according to an embodiment, are trimmed (e.g., by filleting, chamfering or any other suitable technique) such that the corners do not catch on dressings or other materials that might be placed in contact with the first and second side members. The edges 129 of the first and second side members, similarly, are ground down (e.g., buffed, radiused) in order to reduce the sharpness of the edges, so that the edges to not catch on or damage dressings or other materials that might be placed in contact with the first and second side members.

The top or upper portions of an embodiment of the first or second side members contains at least one longitudinally scored portion 120, parallel to a longitudinal edge (e.g., an edge that runs perpendicular to the cross-member), to increase flexibility of the primary support structure at that scored portion 120. According to an embodiment, two scored portions 120 are employed such that one scored portion 120 extends from the top portion of the first side member a distance downwards into the first side member and the second scored portion 120 extends from the upper portion of the second side member a distance downwards into the second side member. The scored portions 120 are disposed in a parallel configuration with each other and with a longitudinal edge of the first and second side members. The position, depth and number of the scored portions 120 is chosen to increase or decrease lateral flexibility (e.g., flexibility along a line parallel to the cross-member) of the first and second side members without modifying the polymer from which the apparatus is constructed. For example, the scored portions 120 may extend from a top portion downward into the first side member a distance of approximately 0.8 millimeters. According to other embodiments, the range of the depth of the scored portions 120 may range from 0 millimeters to 1.5 millimeters. According to an even further embodiment, the range may be from 0.5 millimeters to 1 millimeter. According to an even further embodiment, the range may be from 0.7 millimeters to 0.9 millimeters. The scored portions 120 reduce the strength of the polymer at the scored portions 120, allowing the outermost edges of the first and second side portions to be bendable (e.g., acting as wings that can be bent to conform to a patient's arm). One advantage of bending the first and second side portions might be to more readily secure the assembly by surrounding an appendage of a patient with the retaining assembly 80.

According to an embodiment, a retaining assembly 80 having a longitudinally disposed channel 82 therein is configured to removably secure a catheter hub 100 (e.g., catheter adaptor). The retaining assembly 80 is mounted to the center of the top side 62 of the cross-member 60. The retaining assembly 80 is attached to the cross-member 60 so that the catheter hub 100 is held at a 3-degree angle 87 to increase patient comfort. According to various other embodiments, the retaining assembly 80 could hold the catheter hub 100 at any desired angle in relation to the cross-member 60. According to further embodiments, the retaining assembly could hold a catheter hub of any desired size.

According to an embodiment, the retaining assembly 80 has a right side 84 and a left side 85. The position of the retaining assembly 80 in the center of the top side 62 of the cross-member 60 balances the retaining assembly 80 in a central position not only for patient comfort while the catheter apparatus 10 is moved about, but also for aiding removal of backing 30 from an adhesive layer 99 to secure the apparatus 10 to a patient 200 without jarring the position of the catheter assembly, thus further increasing patient comfort. The adhesive for the adhesive layer 99 is selected from a class of adhesives that are suitable for use on human skin. Various adhesives can be chosen for various embodiments depending on the degree of adhesion required and other factors (e.g., type of skin to be used on, length of time the adhesive must remain adhered).

According to an embodiment, an indention 90 in the rear edge 72 of the cross-member 60 and adjacent to the retaining assembly 80 is optionally configured to allow a catheter hub 100 to be removably secured within the channel 82. Optionally, an indention 90 increases the ease with which a catheter hub 100 is inserted into the retaining assembly 80. Insertion of a catheter hub 100 in to the retaining assembly 80 is aided by the presence of the indention 90 in the cross-member 60 when compared to a retaining assembly 80 affixed to a cross-member 60 without the indention 90.

According to an embodiment, the retaining assembly 80 has a plurality of retaining fingers 110 that mount to the right side 84 and the left side 85 of the retaining assembly 80. These retaining fingers 110 (e.g., retaining members) may number four, and may be positioned at a longitudinal end of the retaining assembly 80. The retaining fingers extend away from the right side 84 and the left side 85 in a circular manner, essentially "grabbing" a catheter hub 100 as it is inserted into the retaining assembly 80, and acting to securing the catheter hub 100, preventing the catheter hub 100 from being removed from the retaining assembly 80.

According to an embodiment, a three-dimensional support structure 112 surrounds, and is integrated (e.g., molded) or otherwise part of the retaining assembly 80. The support structure 112 includes a substantially triangular, sloped element 114 integrated into both sides of the retaining assembly 80 in order to integrate the retaining assembly 80 with the cross-member 60 and prevent it from moving in relation to the catheter apparatus 10. In addition to physically supporting the retaining assembly 80, the sloped elements' primary sloped surface 116 is adapted to receive an adhesive backed surface of aseptic tape or of an aseptic dressing, so that the adhesive backed surface can be adhered (e.g., sealed) substantially continuously to the sloped surfaces, forming a shield between the surrounding environment and the retaining assembly, preventing bacteria from reaching the catheter insertion site.

Figure 6:
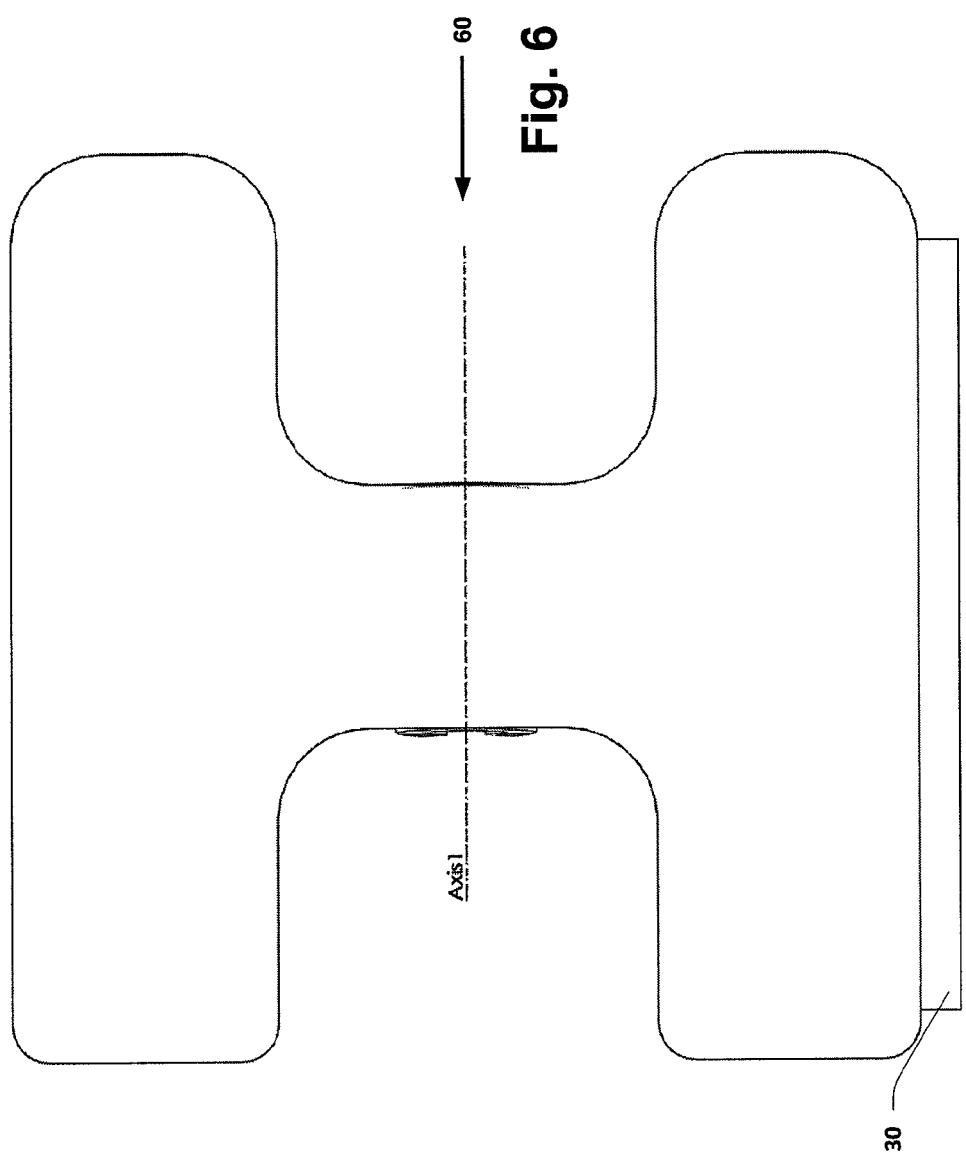
FIG. 6 is a schematic bottom view of an embodiment.
Figure 7:
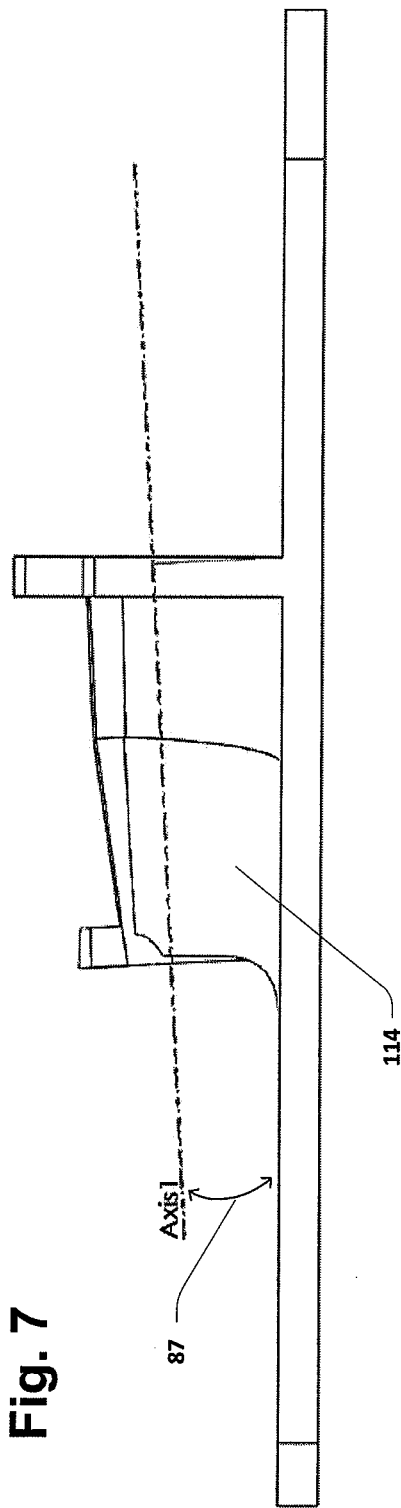
FIG. 7 is a schematic right side view of an embodiment.

According to an embodiment, a first gripping tab 50 is mounted to the top side 62 of the cross-member 60 in vertical relation thereto and between the retaining assembly right side 84 and the outer first edge 66 of the cross-member 60. The first gripping tab 50 has a front side 51, a rear side 52 and a bottom edge 53. The bottom edge 53 is affixed to the top side 62 of the cross-member 60 in parallel position in relation to the front edge 70. A rigid second gripping tab 55 mounted to the top side 62 of the cross-member 60 in vertical relation thereto and between the retaining assembly 80 left side 85 and the outer second edge 68 of the cross-member 60. The second gripping tab 55 has a front wall 56, a rear wall 57, and a lower edge 58. The lower edge 58 is affixed to the top side 62 of the cross-member 60 in parallel position in relation to the front edge 70. The gripping tabs reduce the risk of contaminating the catheter by preventing direct contact of the operator's fingers with the catheter itself. Thus, the risk of infecting a patient 200 is mitigated. The use of the gripping tabs 50, 55 for advancing the catheter apparatus 10 and associated cannula guide needle 101 into the patient's 200 vein reduces the likelihood of contamination and potential for patient infection. In an embodiment, each of the first gripping tab 50 and the second gripping tab 55 have a triangular prism shape which has the same footprint as the preferred embodiment first gripping tab 50 and the second gripping tab 55. In this embodiment each of the first gripping tab 50 and the second gripping tab 55 have an internal cavity 54 therein and a rectangular front side 51, 56 perpendicular to the cross-member 60, as shown in FIG. 6. During use the front side 51, 56 of each of the first and second gripping tabs 50, 55 faces the user.

According to an embodiment, a vertical tab 118 is mounted to the top side 62 of the cross-member 60, the first side member 20 and the second side member 40, in vertical relation thereto, and between the outer side 28 of the first side member and the outer edge 48 of the second side member. The vertical tab 118 has one or more longitudinally scored portions 120, each perpendicular to the cross-member 60 and positioned adjacent to the scored portions 120 in the first side member 20 and the second side member 40. The width of the longitudinally scored portions 120 matches the width of the scored portions 120 in the first side member 20 and the second side member 40. The vertical tab 118 is integrally mounted around the retaining assembly 80 such that it does not interfere with access to the channel 82 of the retaining assembly 80. The vertical tab 118 has a front face 122, a rear face 124, and a bottom edge surface 126. The bottom edge surface 126 is affixed to the top side 62 of the cross-member 60, the first side member 20 and the second side member 40 in parallel position in relation to the front edge 70. The front face 122 of the vertical tab 118 is adapted to receive the adhesive backed surface of aseptic tape or of an aseptic dressing, so that the adhesive backed surface can be adhered substantially continuously to the vertical tab 118. Combined with the sloped elements 114, a shield may be formed around the retaining assembly 80, preventing foreign particles (e.g., bacteria) from entering the catheter insertion site, and also possibly preventing infection.

According to an embodiment, the vertical tab 118 also reduces the risk of contaminating the catheter hub 100 by preventing direct contact of the operator's fingers with the catheter hub 100 or catheter itself. Thus, the risk of infecting a patient 200 is reduced. The use of the rear face 124 of the vertical tab 118 for advancing the cannula guide needle 101 (e.g., placing an operator's fingers only on the rear face 124 in order to advance the guide needle and surrounding cannula) into the patient's 200 vein reduces the likelihood of contamination and potential for patient 200 infection. Additionally, use of only the rear face 124 maintains the front face 122 in an aseptic condition for when a dressing is placed over the retaining assembly 80.

Figure 3:
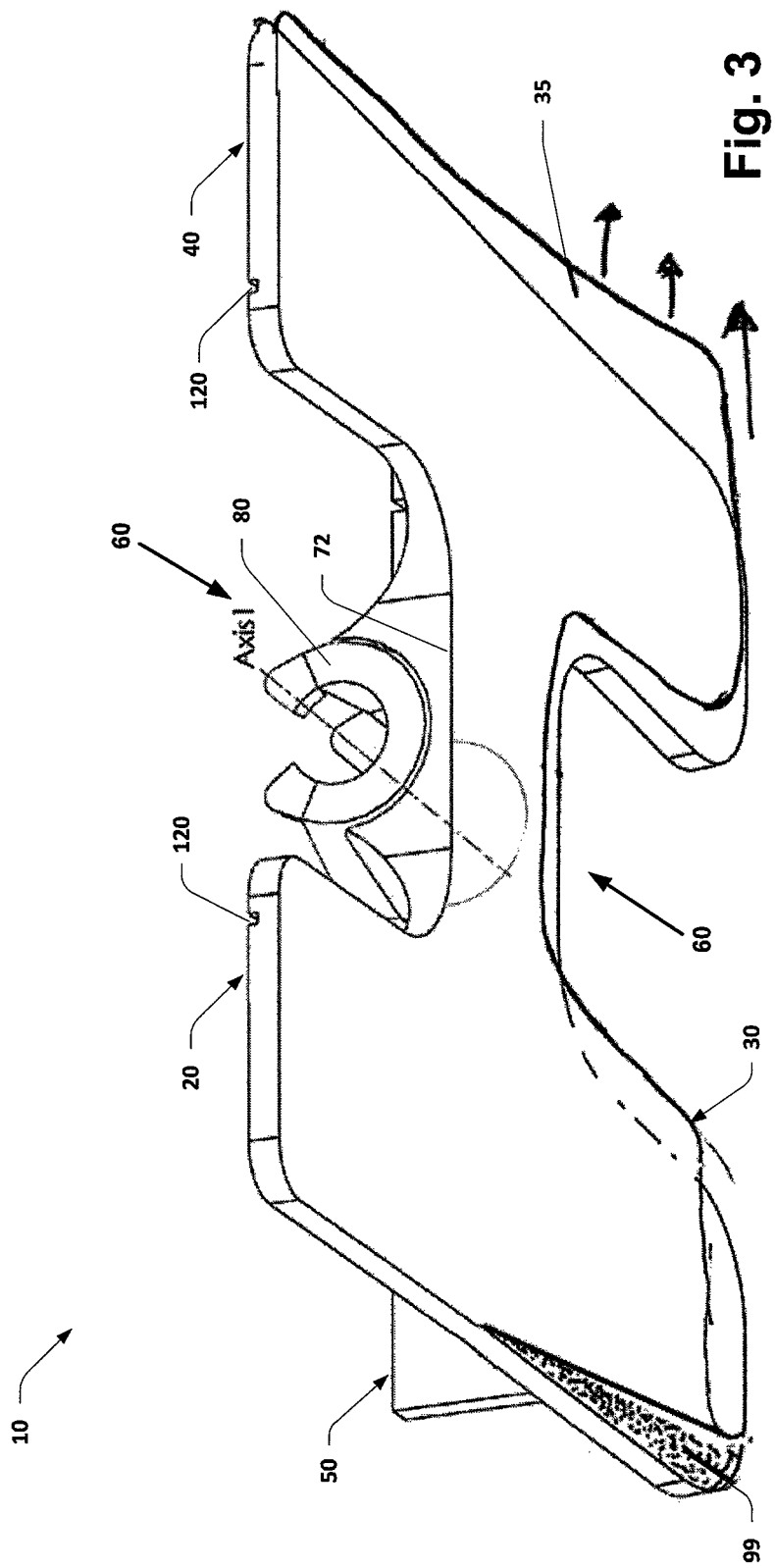
FIG. 3 is a schematic isometric bottom view of an embodiment.
Figure 4:
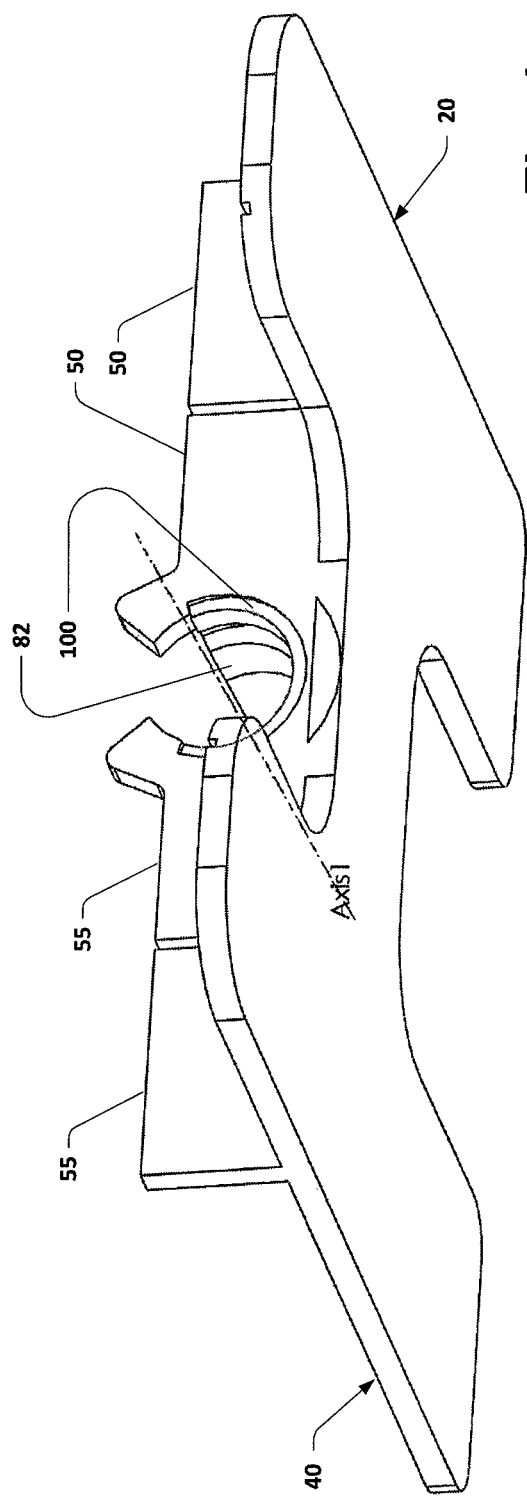
FIG. 4 is a schematic isometric bottom view of an embodiment.
Figure 5:
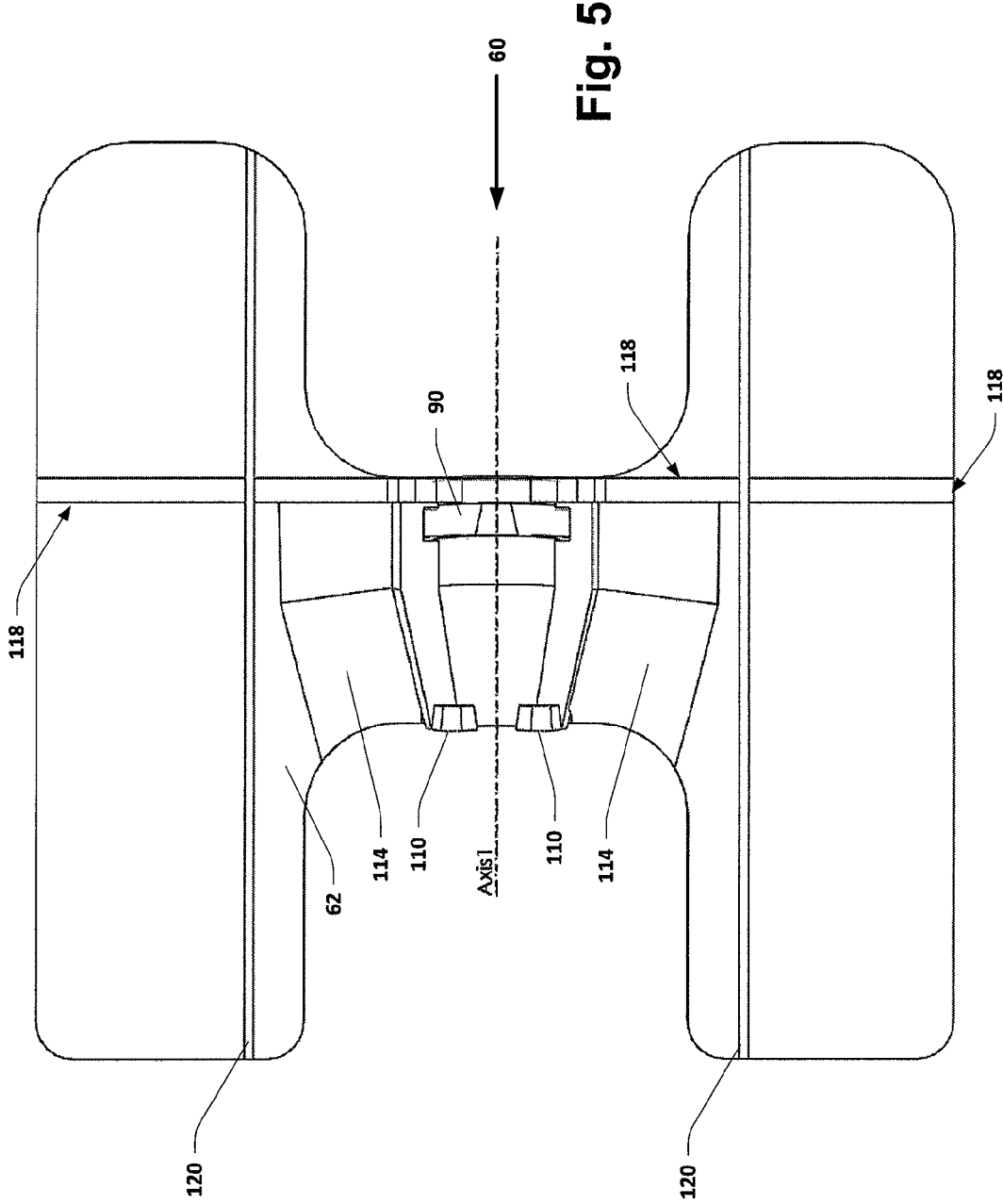
FIG. 5 is a schematic top view of an embodiment.
Figure 8:
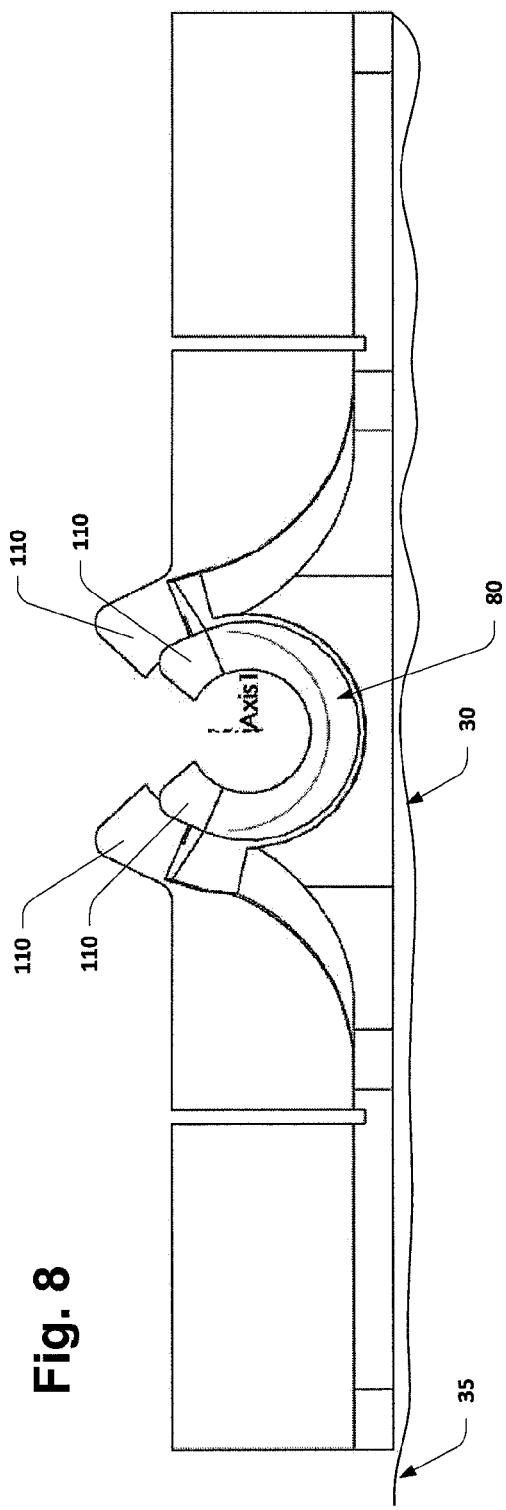
FIG. 8 is a schematic front view of an embodiment.
Figure 18:
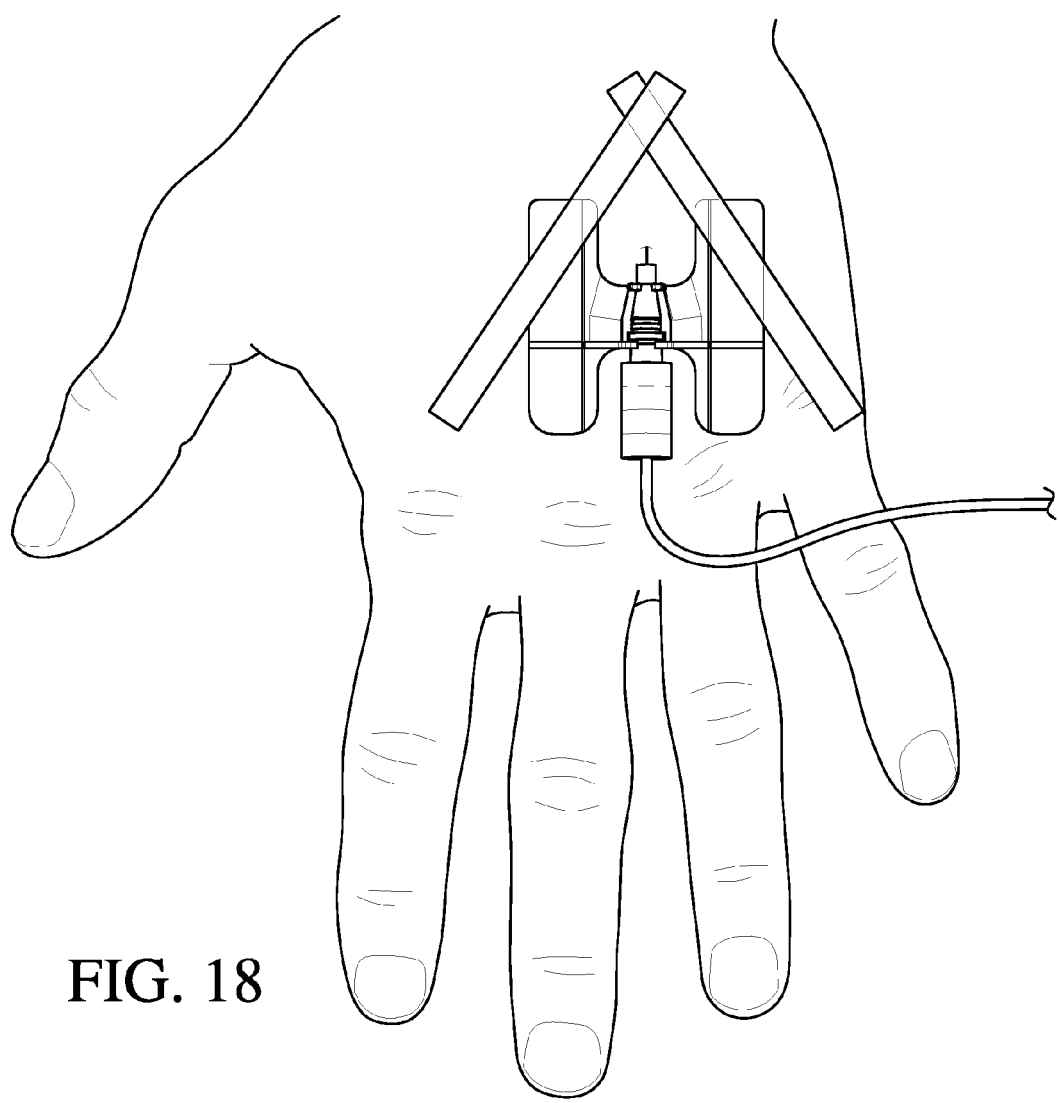
FIG. 18 is a schematic in-use drawing of a method of attaching a providing additional securement to an embodiment with the use of adhesive medical strips.
Figure 19:
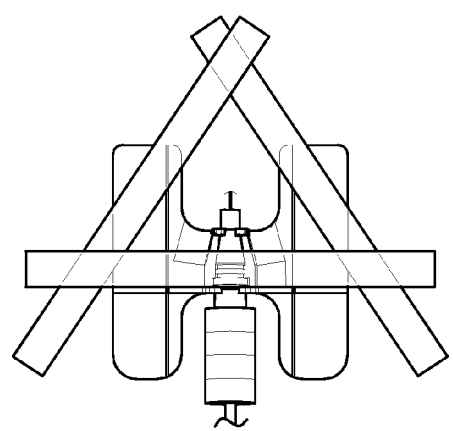
FIG. 19 is a schematic top view of an embodiment additionally secured with adhesive medical strips.
Figure 20:
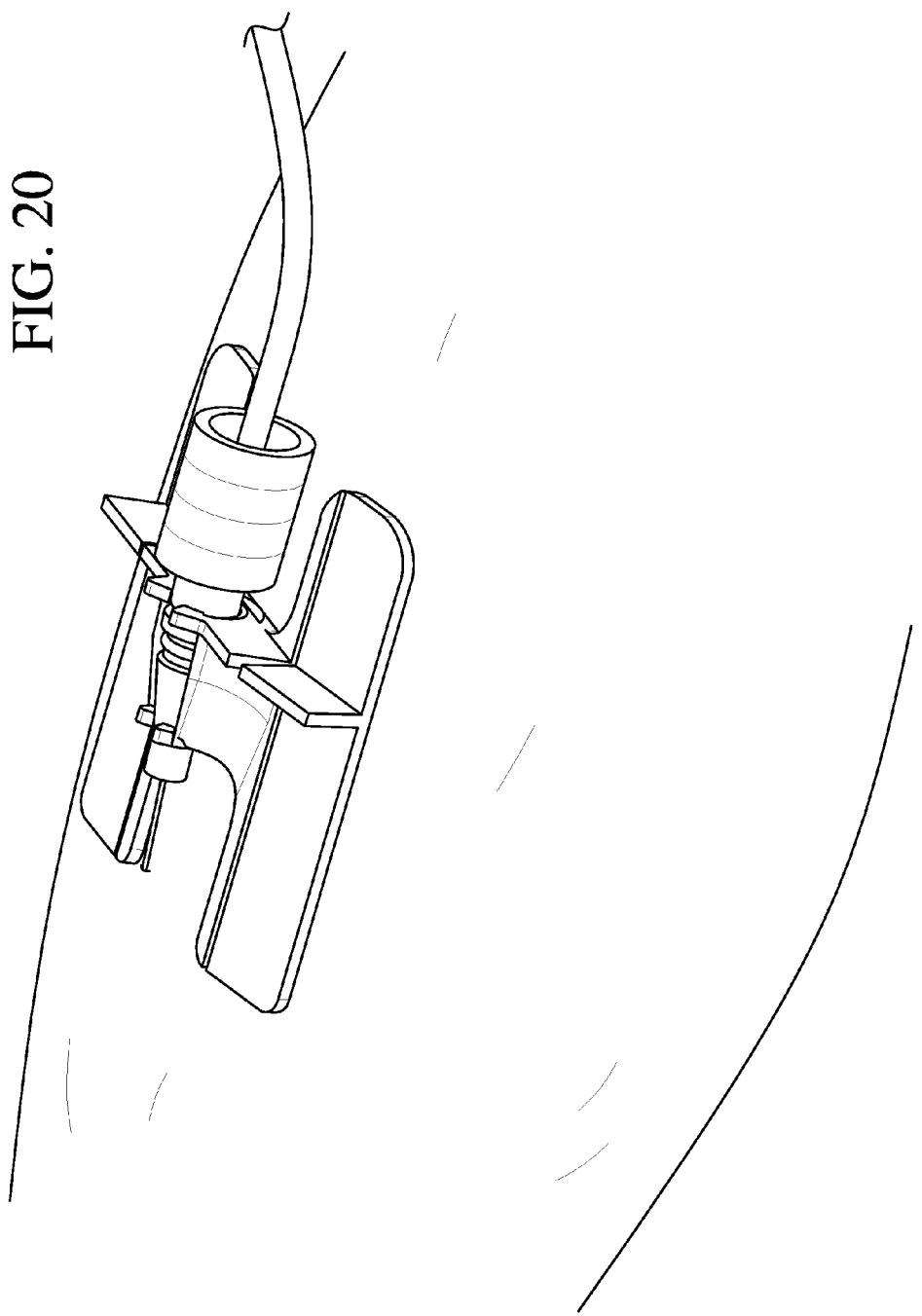
FIG. 20 is a schematic in-use drawing of an embodiment as it is secured to the skin with an adhesive backing, holding the cannula of a catheter hub in place with a medical accessory attached to the catheter hub.
Figure 21:
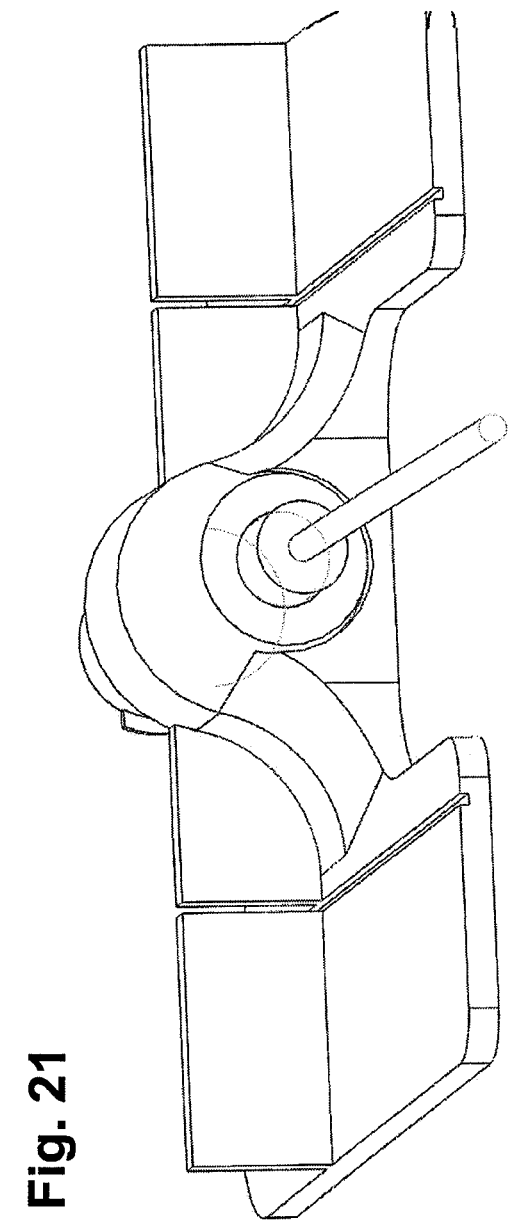
FIG. 21 is a schematic front-right perspective view of an embodiment having an integrated catheter hub and a cannula extending therefrom.
Figure 22:
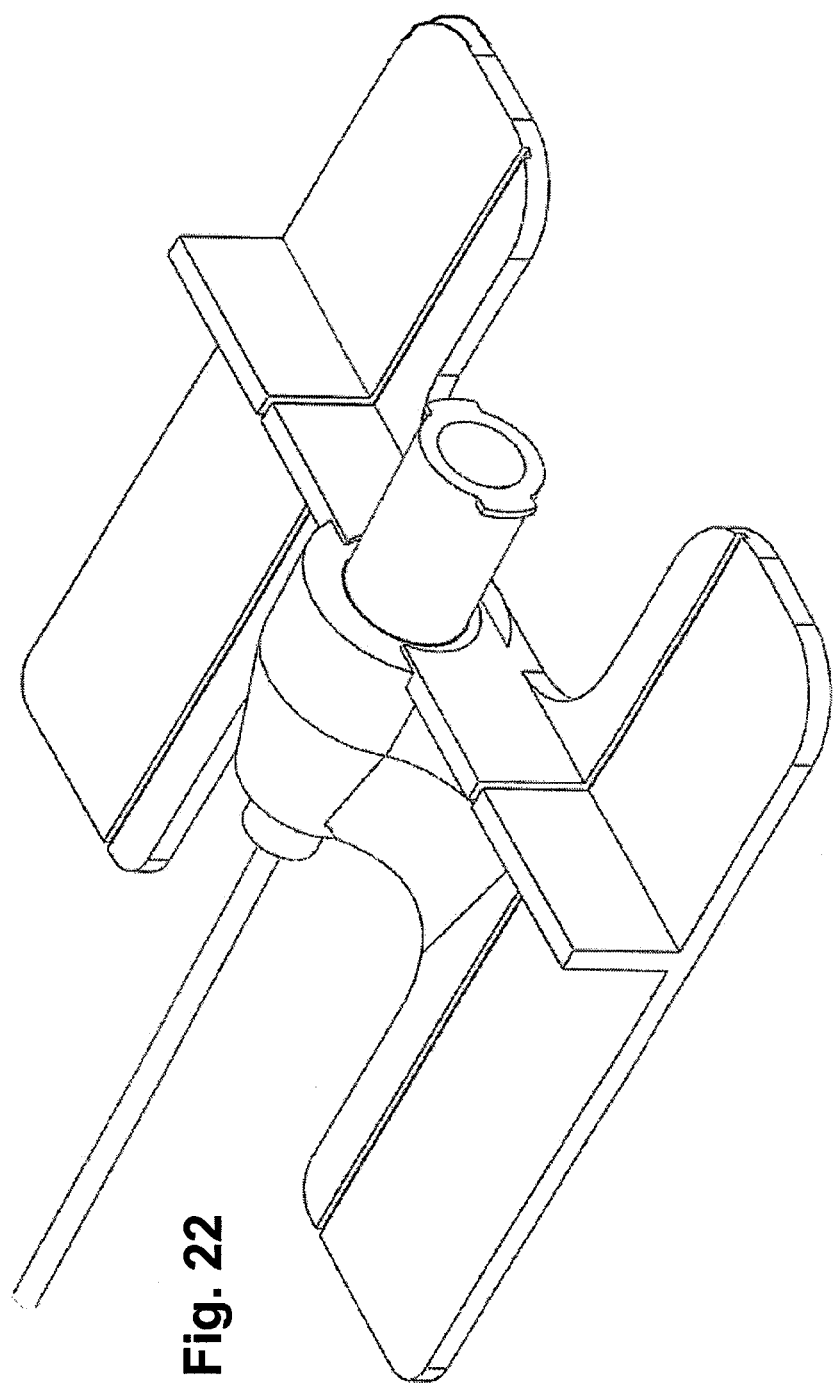
FIG. 22 is a schematic rear-left perspective view of an embodiment.
Figure 23:
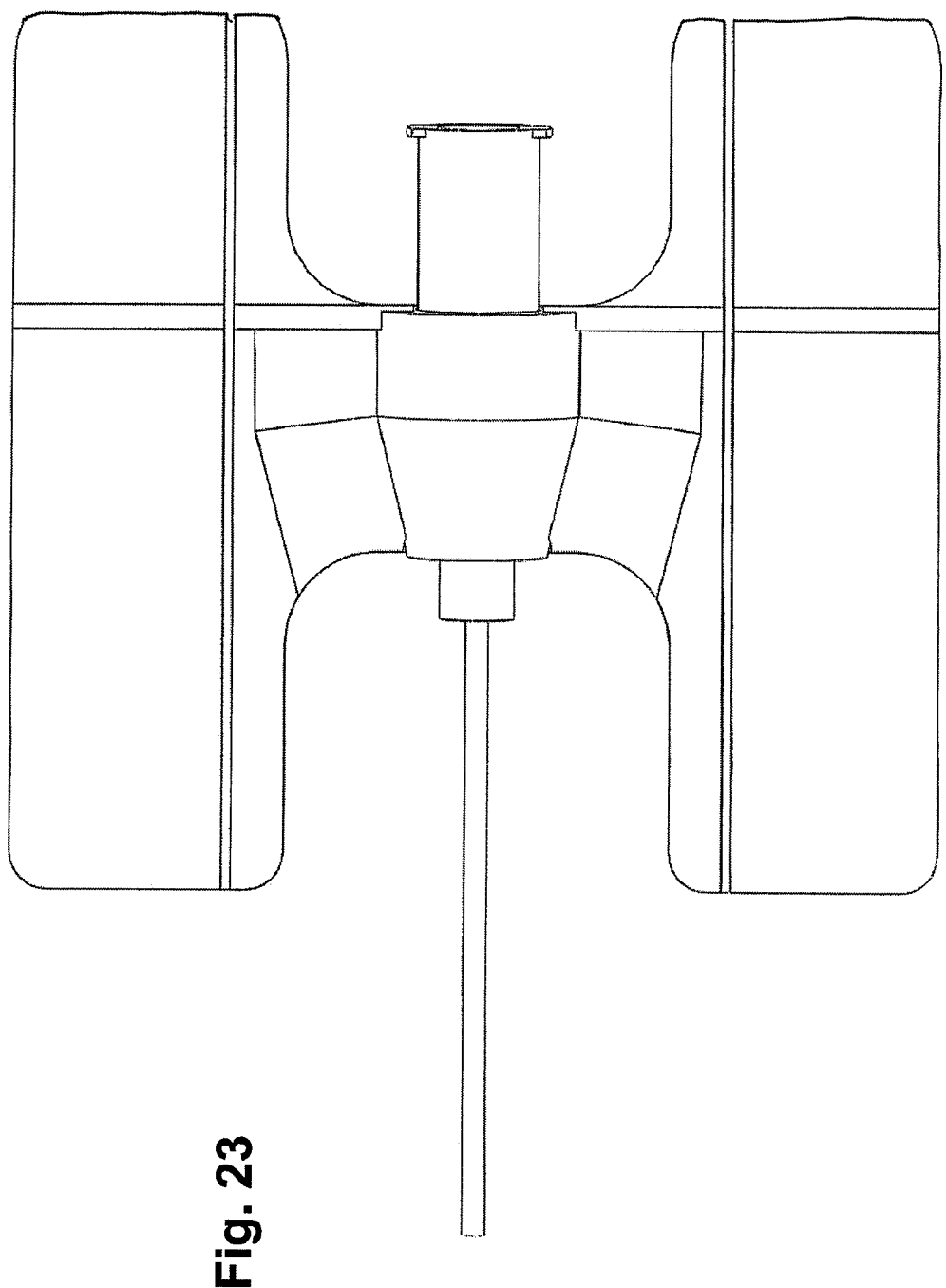
FIG. 23 is a schematic top view of an embodiment.
Figure 24:
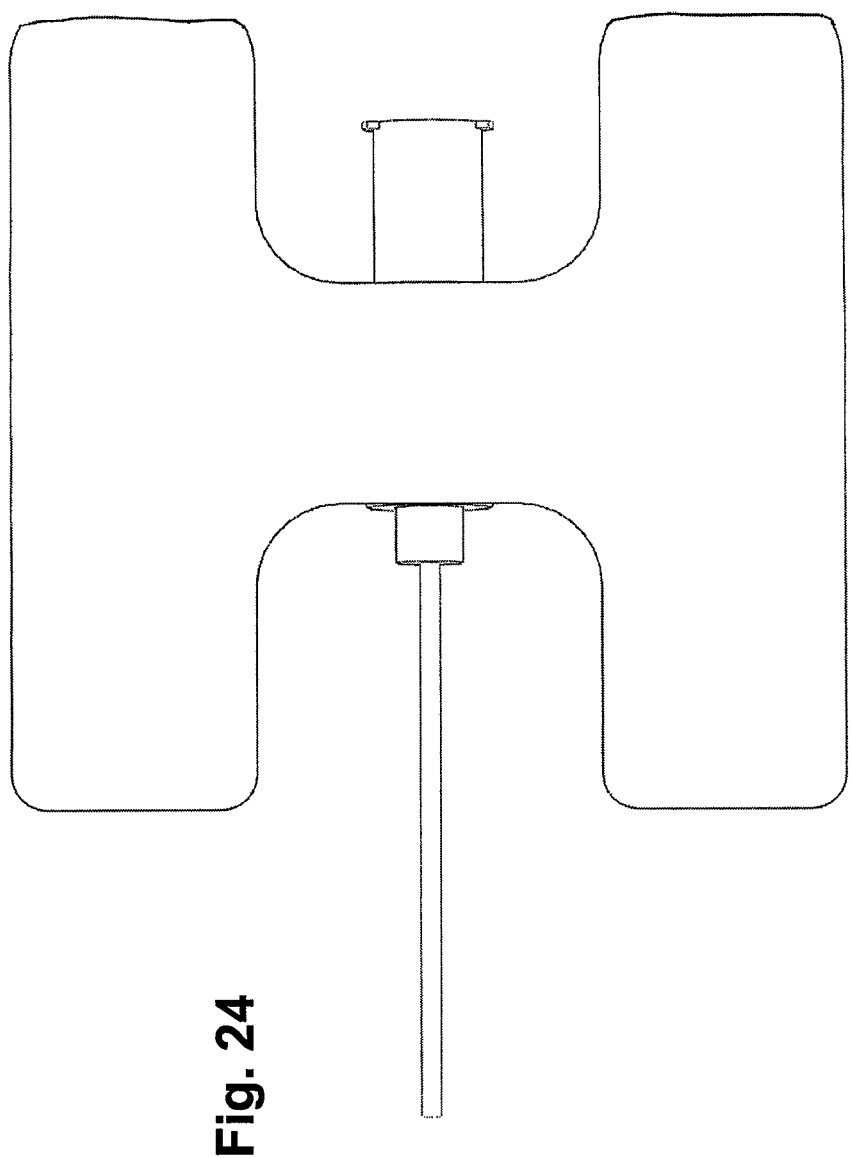
FIG. 24 is a schematic bottom view of an embodiment.
Figure 25:
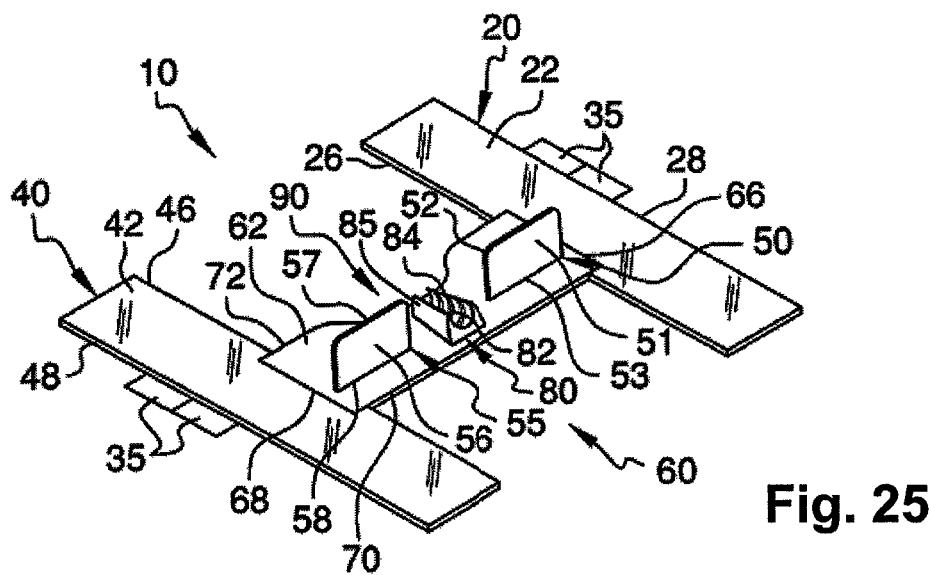
FIG. 25 is an isometric top view of an embodiment.
Figure 26:
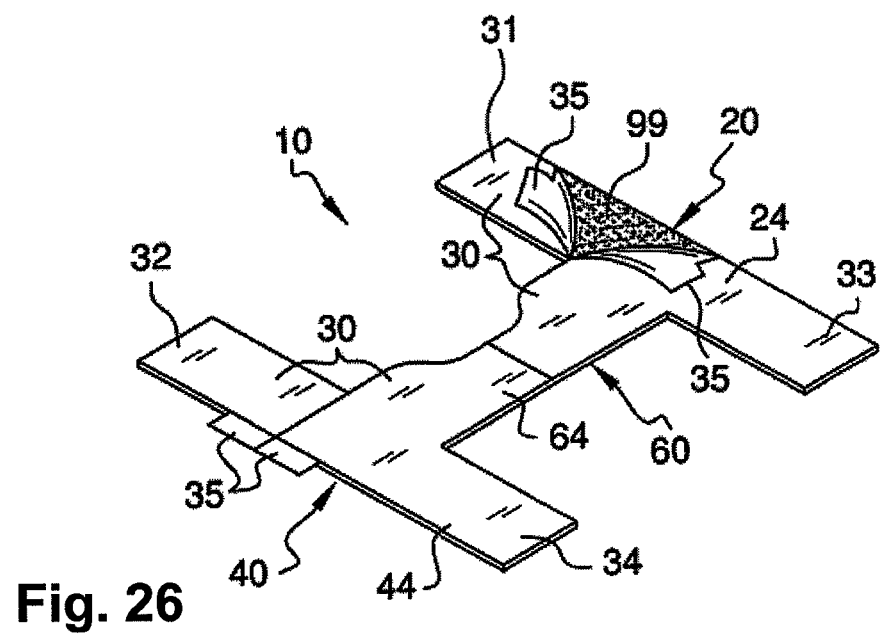
FIG. 26 is an isometric bottom view of an embodiment.
Figure 27:
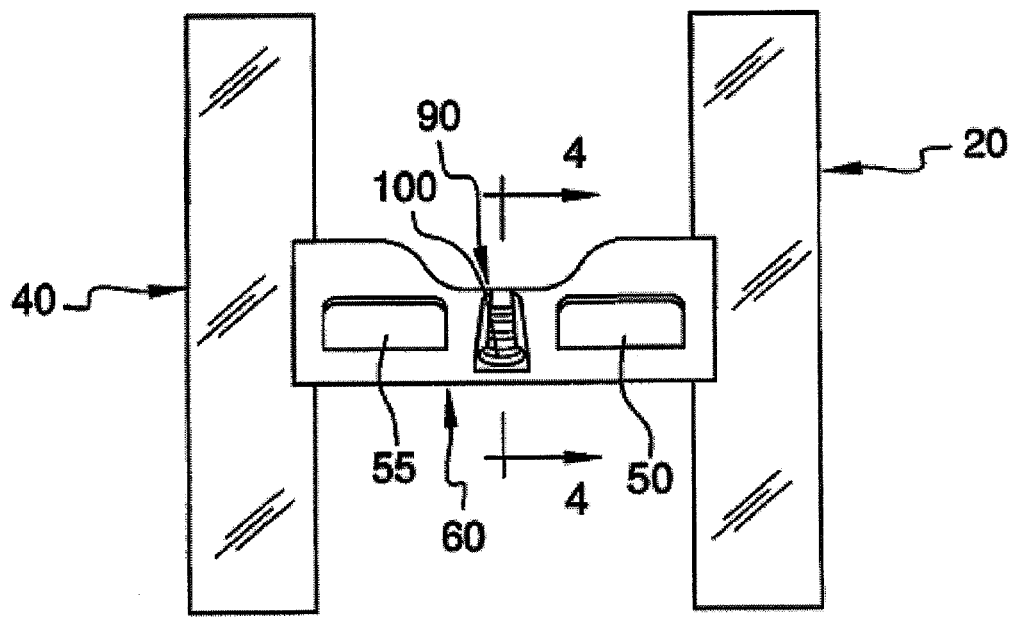
FIG. 27 is a top plan view of an embodiment.
Figure 28:
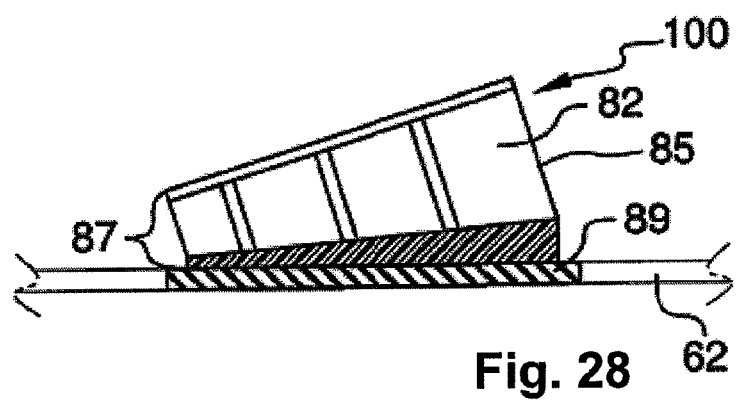
FIG. 28 is a cross-section view of an embodiment taken along line 4-4 of FIG. 27.
Figure 29:
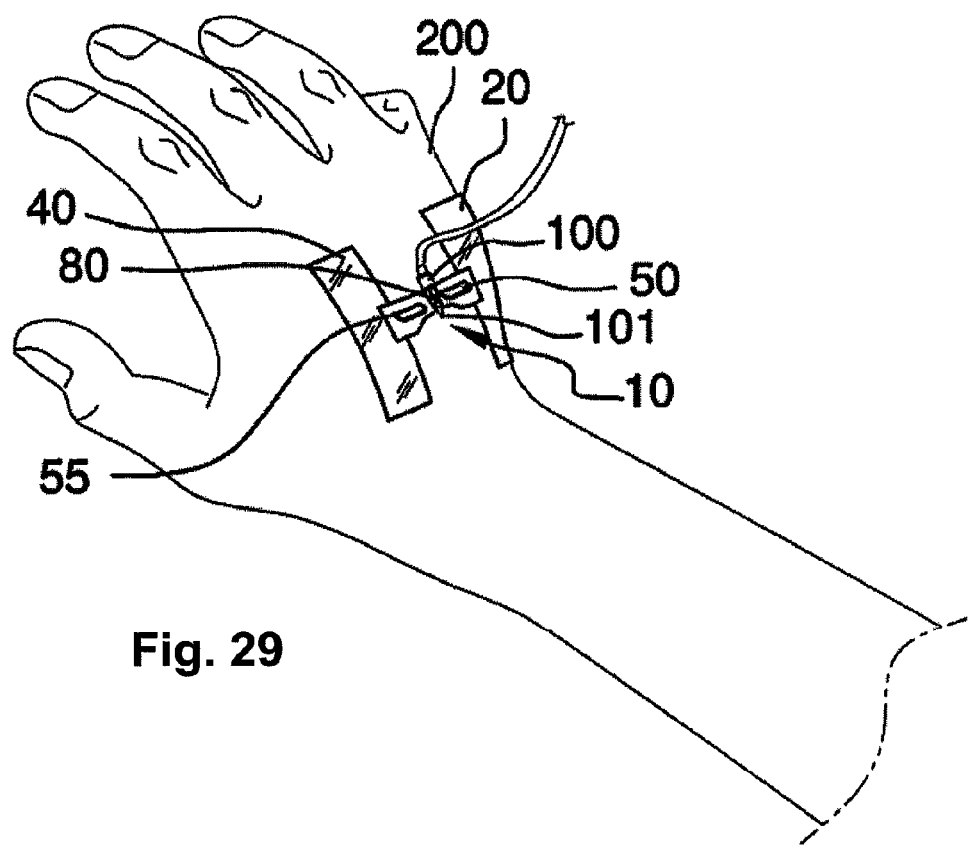
FIG. 29 is an isometric in-use view of an embodiment.
Figure 30:
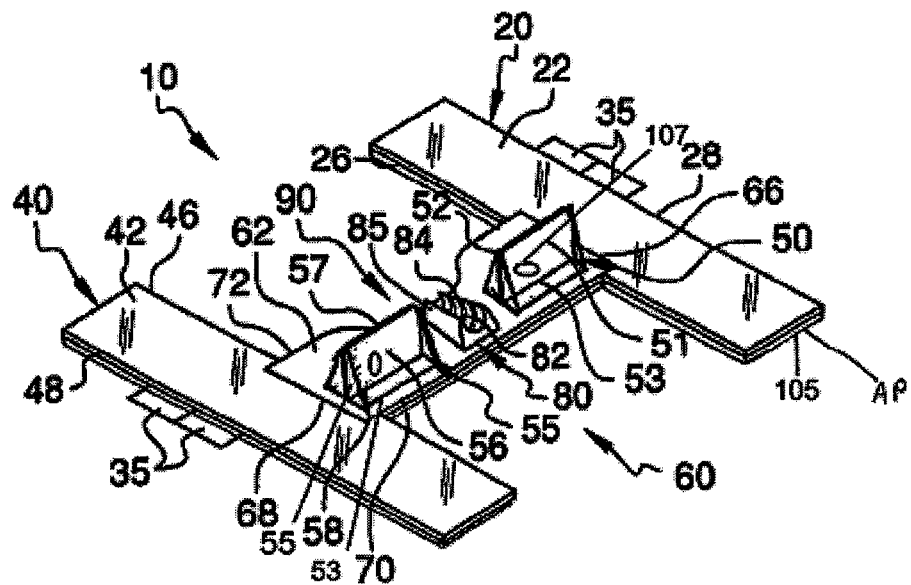
FIG. 30 is an isometric top view of an embodiment.
Figure 31:
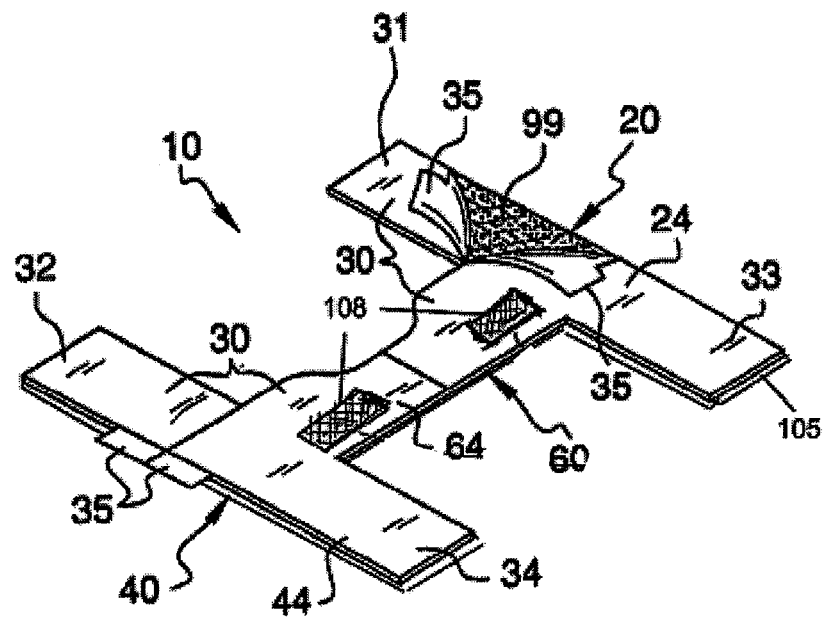
FIG. 31 is an isometric bottom view of an embodiment.

An adhesive layer 99, shown in FIGS. 3, 8 and 26 according to an embodiment, is disposed on the lower portion 24 of the first side member 20, on the bottom portion 44 of the second side member 40, and on the bottom side 64 of the cross-member 60, permits the apparatus 10 to be secured to a patient's skin more quickly and easily than securement with tape, although some embodiments, shown in FIGS. 18 and 19, employ medical tape strips to provide for further securement of the retaining assembly 80 once the adhesive layer is exposed. In an embodiment, a backing 30 may cover the adhesive layer 99 so that the catheter apparatus 10 can be positioned without exposing and seating the adhesive layer 99. The backing 30 may be one continuous backing that is folded over, such that the folded over portion extends to the side of the catheter apparatus 10 opposite the folded over portion, where a backing removal extension piece extends beyond the catheter apparatus 10 for removal of the backing through the act of pulling the backing removal extension piece 35. In an embodiment, an absorbent pad 105, which is disposed on the entire bottom side 64 of the cross-member 60, the first side member 20 and the second side member 40, is substituted for the adhesive layer 99.

According to an embodiment, a pressure-released polymer adhesive-containing capsule 107 is disposed within the internal cavity 54 of each of the first and second gripping tabs 50, 55. Each of the capsules 107 has a diameter of approximately 1/8 inch. According to an embodiment, in use, when securing the alternative embodiment of the apparatus 10 to the patient, the user places pressure on the first and second gripping tabs 50, 55 to break open the capsules 107 therein and to release the polymer adhesive which passes through mesh openings 108 disposed on an bottom edge 53 of each of the first and second gripping tabs 50, 55 to permeate the absorbent pad and then onto user's skin to adhere the apparatus 10 onto the patient's skin. Alternatively, the polymer adhesive is released onto and through the absorbent pad 105 onto the patient's skin and then combines with a second adhesive which has already been applied to the patient's skin, prior to the polymer adhesive, and the combination thereof secures the apparatus 10 onto the patient's skin.

According to an embodiment, a backing 30, which removably covers the adhesive layer 99 has a rectangular first part 31, a rectangular second part 32, a L-shaped third part 33, and a L-shaped fourth part 34. The first part 31, second part 32, third part 33, and fourth part 34, each having a backing removal extension piece 35. In the alternative embodiment, the backing 30 removably covers the absorbent pad 105.

According to an embodiment, an adhesive layer 99 is disposed on the lower portion 24 of the first side member 20, on the bottom portion 44 of the second side member 40, and on the bottom side 64 of the cross-member 60. The adhesive layer 99 may be applied to the lower portion 24, the bottom portion 44, or the bottom side 64 at separate times or at the same time. A backing 30 is disposed on the adhesive layer 99 (e.g., the portion of the adhesive layer opposite the lower portion 24, bottom portion 44, or bottom side 64) such that removal of the backing 30 will expose the adhesive layer 99, enabling an un-backed portion of the apparatus to be adhered to a surface. The backing 30 of the adhesive layer 99 may cover the entire adhesive layer 99 or be scored and separated into multiple portions for ease of de-backing when the apparatus is placed in close proximity to the surface of a patient's skin. One or more backing removal extension pieces 35 of the backing 30 may extend past an edge of the apparatus so that an operator can grasp the backing removal extension piece 35, and easily remove the backing 30 from the adhesive layer 99 underneath.

According to an embodiment, a spring-loaded push-release button 110 is disposed atop an attachment end of a plastic housing 112 into which the cannula guide needle 101 is retracted.

Figure 13A:
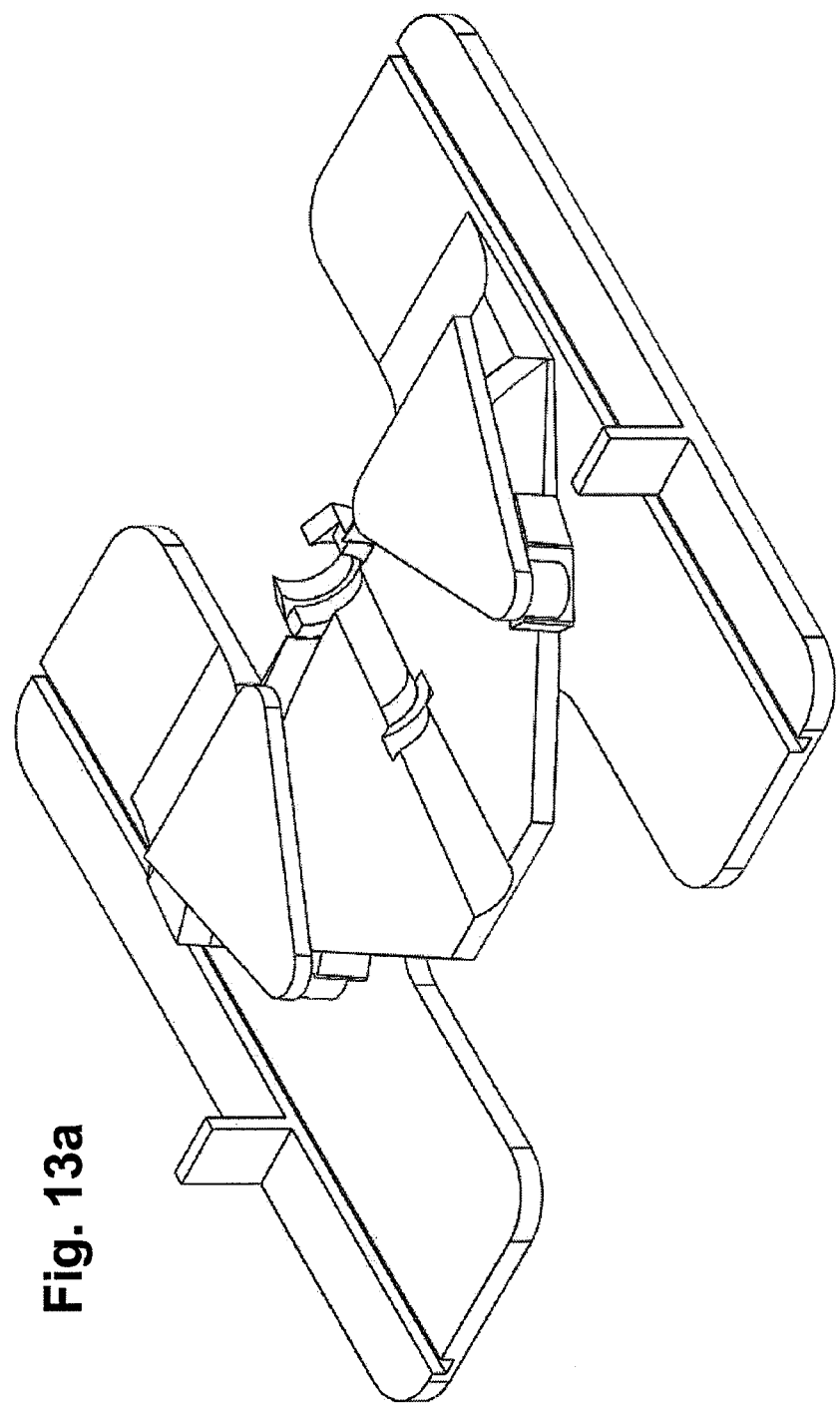
FIG. 13a is a schematic isometric top view of an embodiment containing a winged catheter hub attachment.
Figure 13B:
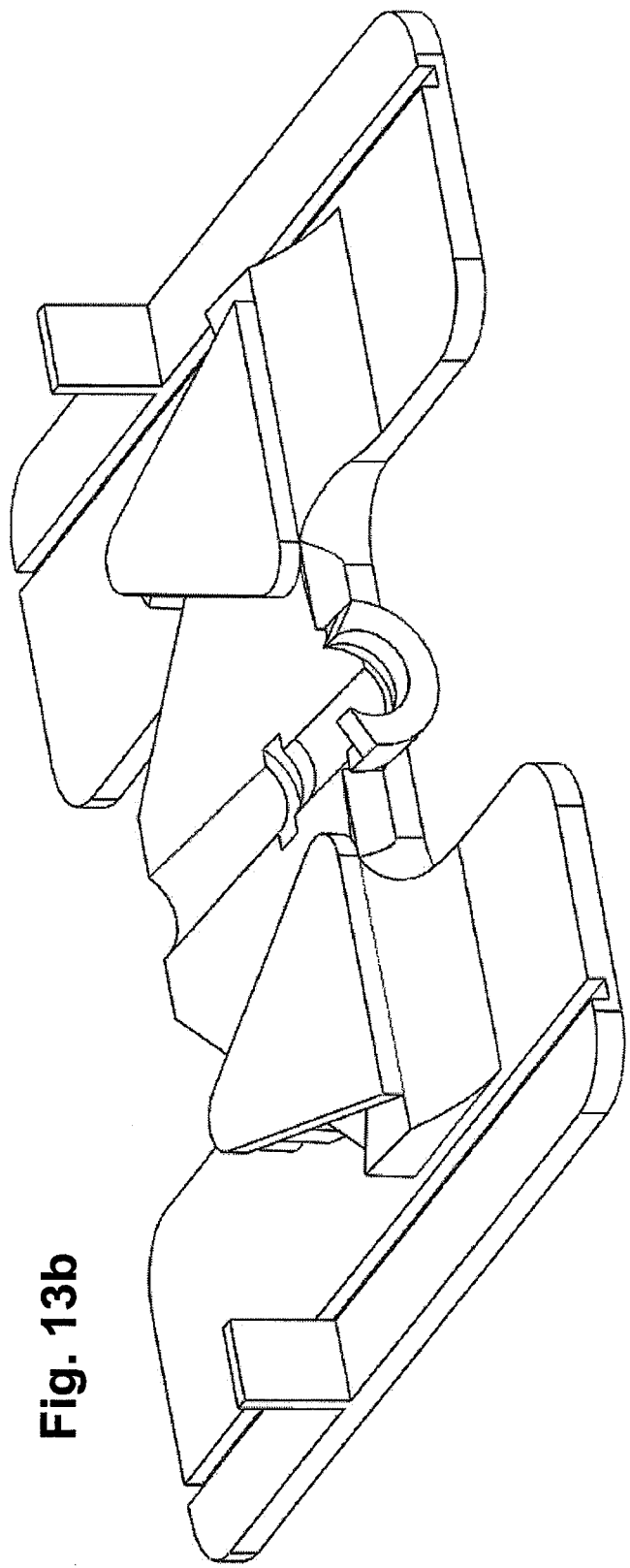
FIG. 13b is a schematic perspective rear view of an embodiment containing a winged catheter hub attachment.

An embodiment that can be used with a catheter having winged attachments, such as the BD Nexiva™ brand closed IV catheter system, commercially available from Beckton, Dickinson and Company of Franklin Lakes, N.J., is shown in FIGS. 13a through 13c.

Operation, According to Various Embodiments

Figure 9:
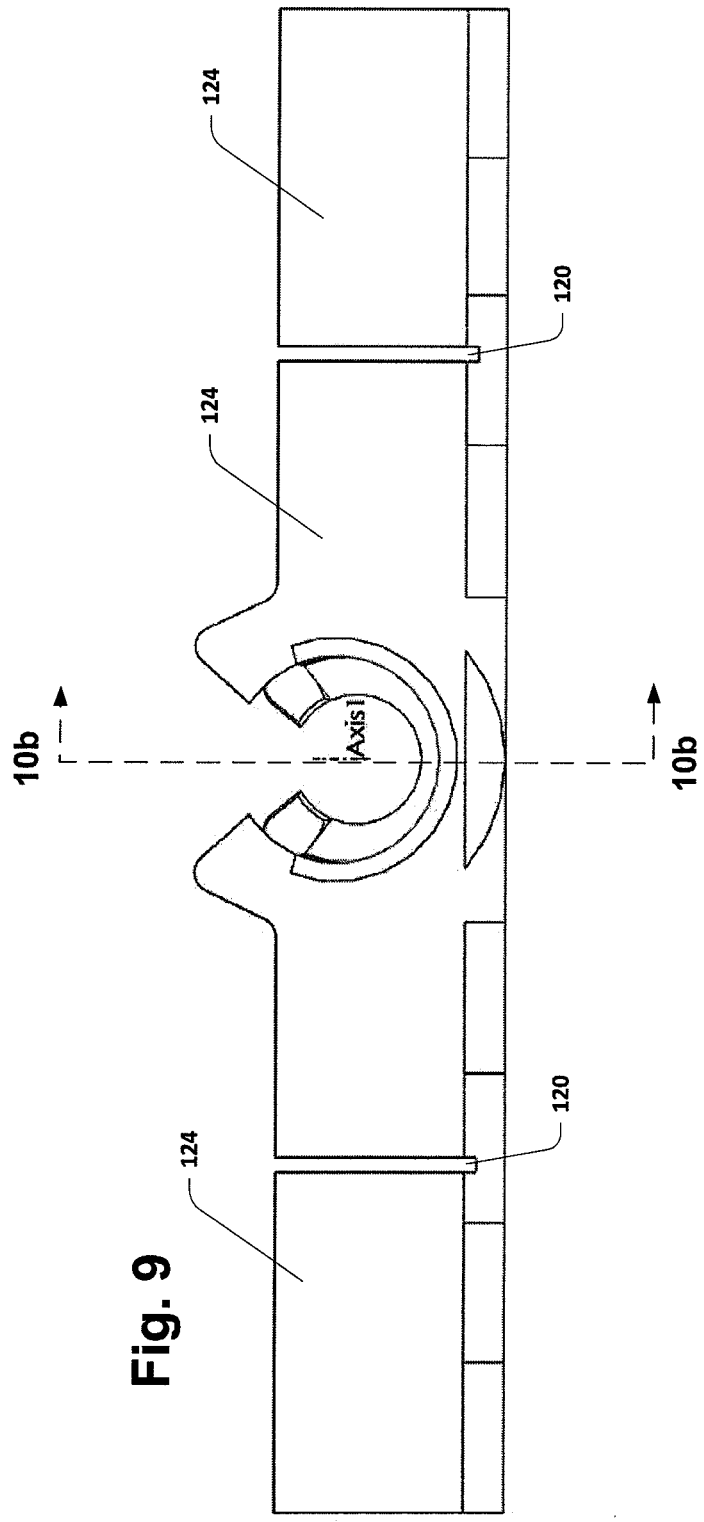
FIG. 9 is a schematic back view of an embodiment.
Figure 10A:
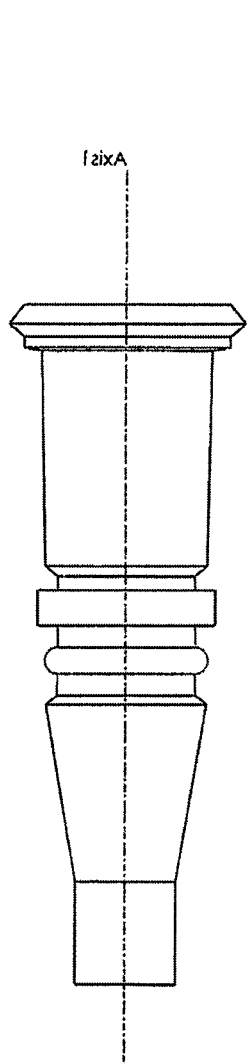
FIG. 10a is a schematic side view of a catheter hub according to an embodiment.
Figure 10B:
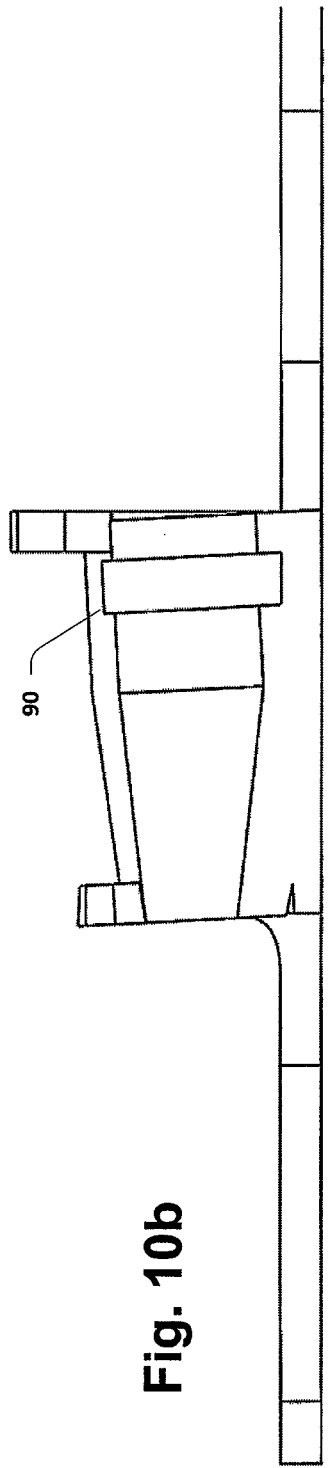
FIG. 10b is a cross sectional view along the line 10b-10b of FIG. 9.
Figure 11:
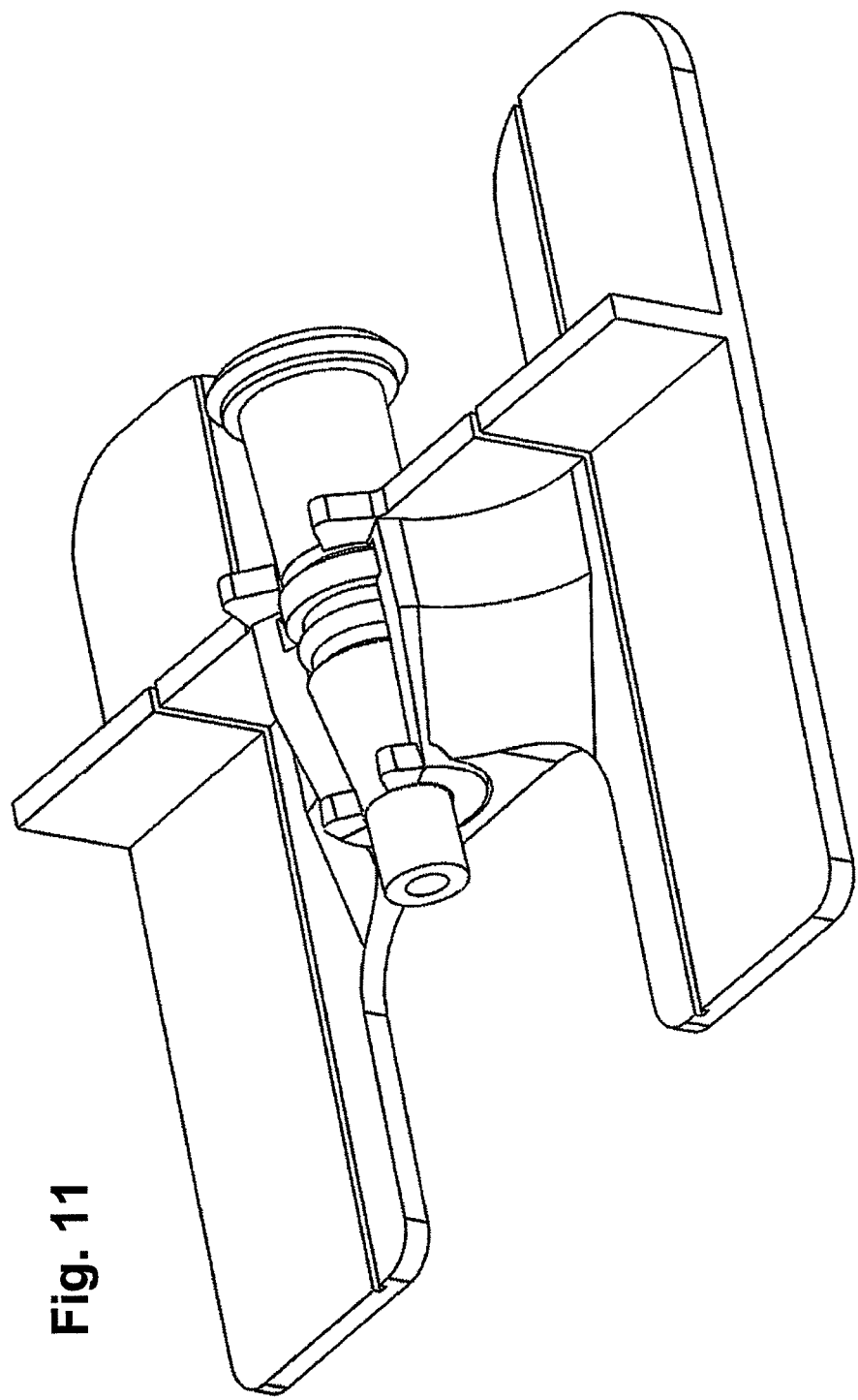
FIG. 11 is a schematic isometric top view of an embodiment having a catheter hub inserted therein.
Figure 14:
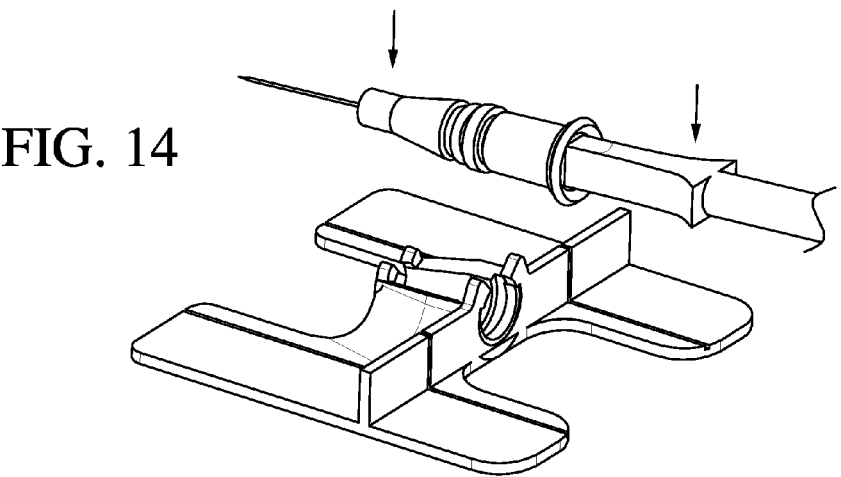
FIG. 14 is a schematic in-use drawing of a catheter hub and associated cannula and need being snapped into an embodiment.
Figure 15:
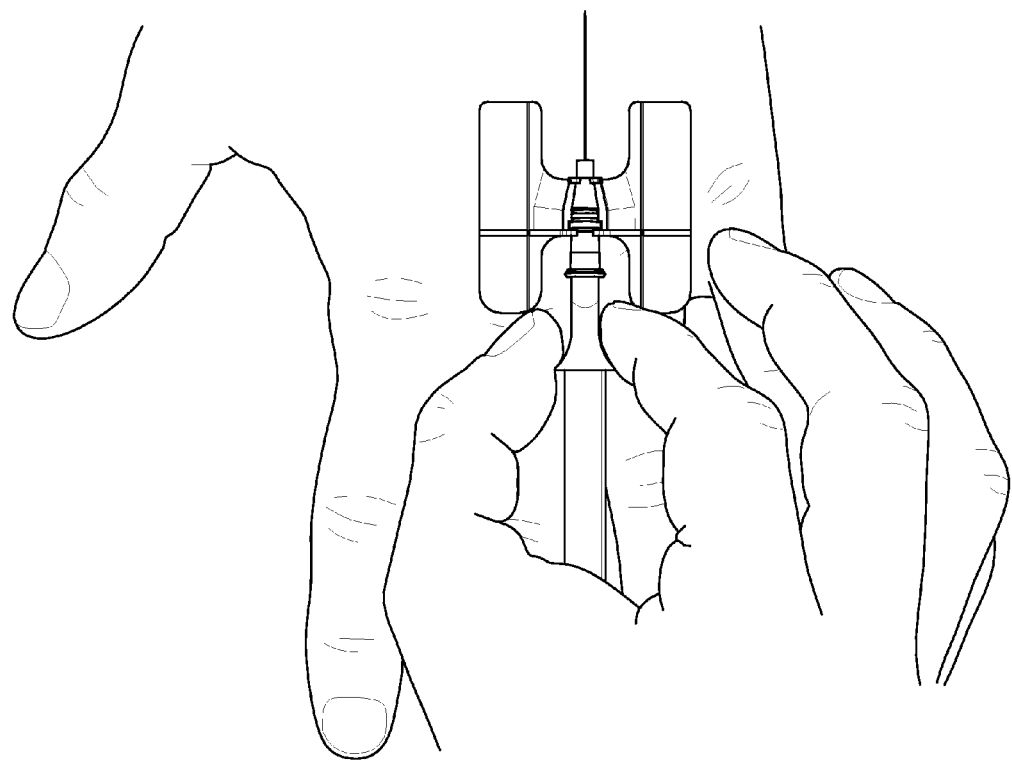
FIG. 15 is a schematic in-use drawing of a method for locating the needle of a catheter on the surface of a patient's skin, according to an embodiment.
Figure 16:
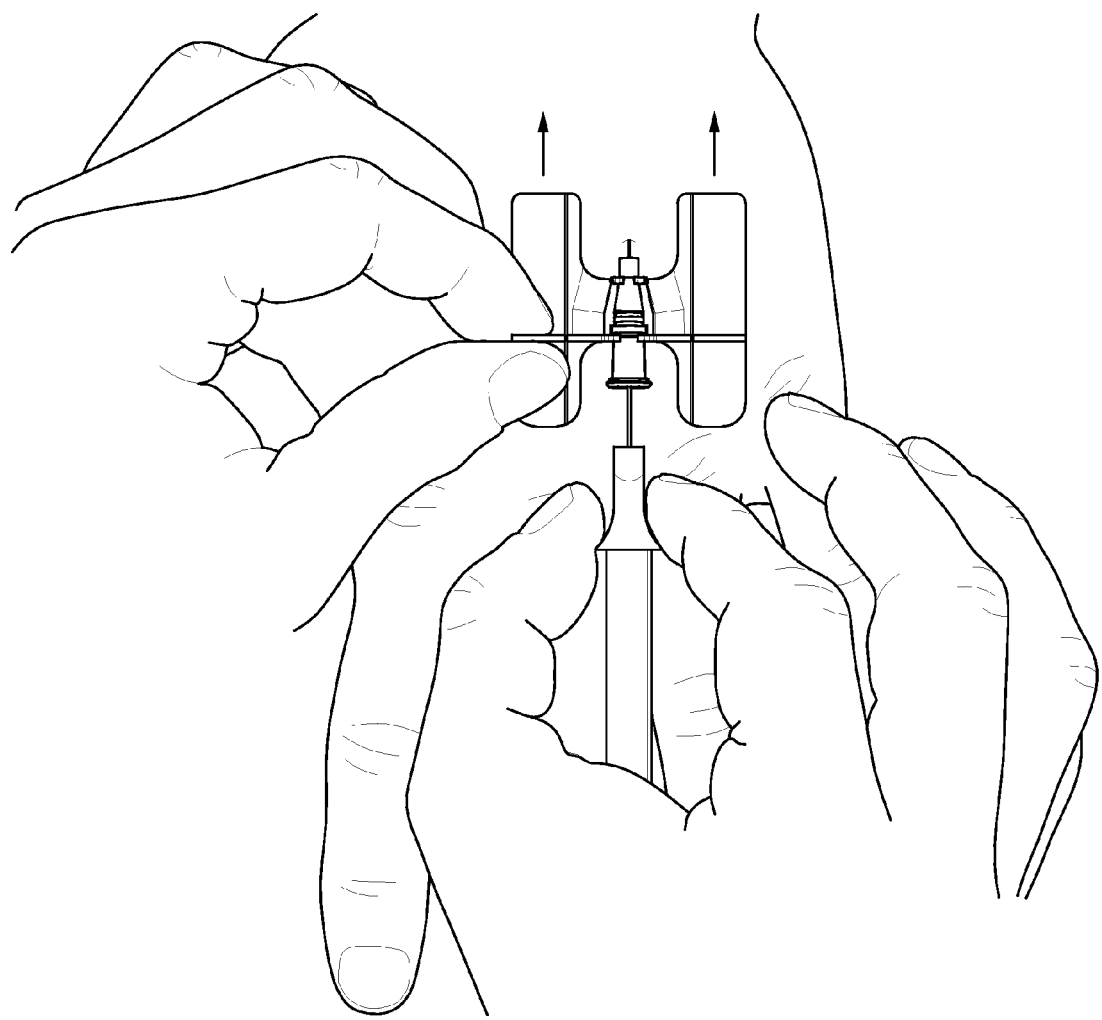
FIG. 16 is a schematic in-use drawing of a method for removing the needle while advancing the cannula of the catheter into a patient's skin, according to an embodiment.
Figure 17:
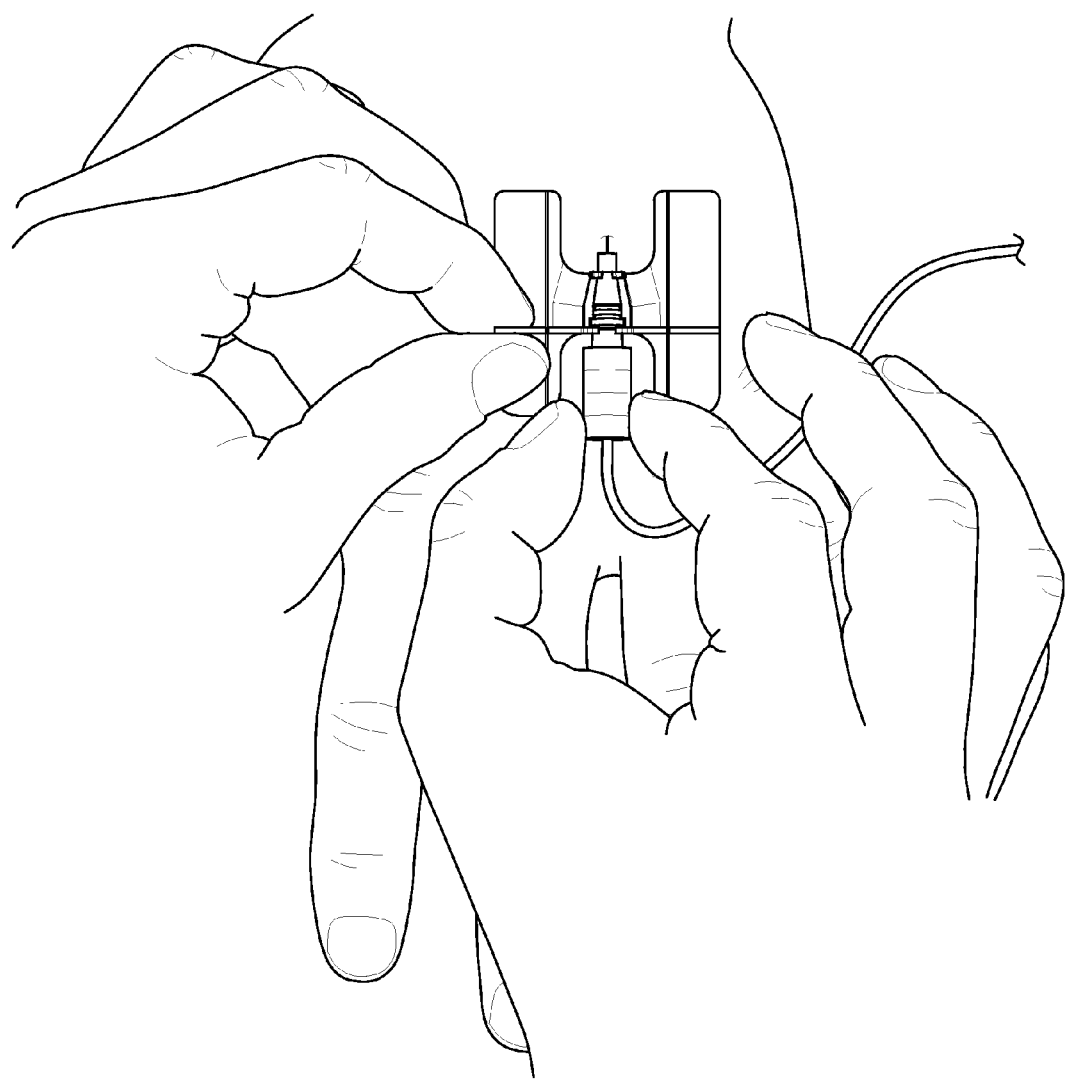
FIG. 17 is a schematic in-use drawing of a method of attaching a medical accessory to the catheter hub, according to an embodiment.

As shown in FIGS. 14 through 20, according to an embodiment, to use the present apparatus 10, an operator, such as a nurse or physician, begins by placing a catheter hub 100 securely into the retaining assembly 80 before inserting an attached cannula guide needle 101 into a patient. FIG. 9 shows a rear view of the catheter apparatus 10, and FIG. 10b shows a cut-away view of FIG. 9, along the line 10-10. FIG. 10a shows the catheter hub and FIG. 10b shows where the catheter hub 100 is to be received. FIG. 11 shows an example of one type of catheter hub that can be secured by the catheter apparatus 10. FIGS. 12 and 14 shows that hub inserted into the retaining assembly of the catheter apparatus 10. The operator then proceeds by locating and piercing the patient's 200 vein with a cannula guide needle 101 of the catheter hub 100. Then, gripping either the first gripping tab 50 or second gripping tab 55, an operator advances the cannula guide needle 101 into a patient's 200 vein. After the cannula guide needle and associated cannula is desirably inserted into the vein, the operator grips either the first gripping tab 50 or second gripping tab 55, depending on the operator's dominant hand, while attaching corresponding I.V. tubing with the operator's other hand.

According to an embodiment, to secure the apparatus 10 to the patient's skin, the operator slightly lifts the cross-member 60 while removing the backing 30 by pulling on the backing extension piece 35. After removing the backing 30, the user presses down on the cross-member 60, first side member 20, and second side member 40 to secure the apparatus 10 to a patient 200.

According to an embodiment shown in FIGS. 14 through 20, a user selects a site on the patient 200 for the site of the catheter (e.g., and catheter apparatus 10) and prepares the site according to a predetermined procedure. A tourniquet is applied to the arm of the patient 200 at a point above the IV insertion point. The catheter hub 100 of an intravenous catheter (e.g., still attached to the I.V. starting device, such as a cannula guide needle 101) is placed into the retaining assembly 80 where it becomes removably attached to the catheter apparatus 10. With the catheter apparatus 10 and catheter hub 100 assembled, the vein is pierced with the cannula guide needle 101. A thumb and forefinger can then be used to grasp the vertical tab 118 on either side of the catheter hub 100 so that a force in the direction of the vein can be applied to the catheter apparatus 10, causing the catheter (e.g., the cannula of the catheter and the cannula guide needle) to advance into the vein. At this point, the catheter assembly will be resting on the skin of the patient. As the cannula guide needle 101 is retracted, the catheter apparatus 10 is held in place by the vertical tab 118. Ancillary catheter tubing is then secured, and the tourniquet is removed from the arm of the patient 200. The catheter apparatus 10 is secured when the user pulls on the backing removal extension piece 35, uncovering the adhesive layer on the underside of the catheter apparatus 10, enabling the adhesive layer to come into contact with the skin.

According to an embodiment, addition securement can be provided by placing securement tape (e.g., steri-strips, medical tape strips) over the apparatus 10 and the attached catheter hub 100. An example of one method of providing additional securement to the apparatus is shown in FIG. 19.

According to other embodiments, for securing the device to the patient's skin, the user slightly lifts the cross-member 60 while removing the backing 30 from the lower side 109 of the absorbent pad 105 by pulling on a corresponding extension piece. The user then places pressure on the first and second gripping tabs 50, 55 to break open the capsules 107 and to release the polymer adhesive through the mesh openings 108 to permeate the absorbent pad, and then onto to the user's skin to adhere the apparatus 10 onto the patient's skin. Alternatively, the polymer adhesive is released onto and through the absorbent pad 105 onto the patient's skin and then combines with a second adhesive which has already been applied to the patient's skin, prior to the polymer adhesive, and the combination thereof secures the apparatus 10 onto the patient's skin. To retract the cannula guide needle, the user pushes the spring-loaded push-release button 110 disposed atop an attachment end of the plastic housing 112 in some embodiments.

FIGS. 21 through 24 illustrate an embodiment in which the catheter apparatus 10 is an integrated part of a catheter, such that the catheter hub 100 is integrated into (e.g., molded into) the apparatus 10. A cannula is shown extending from an end of the catheter hub, ready for insertion into a vein of a patient.

The word "exemplary" is used herein to mean serving as an example, instance, or illustration. For the avoidance of doubt, the subject matter disclosed herein is not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

In view of the exemplary apparatus and methods described supra, methodologies that may be implemented in accordance with the disclosed subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter.

While the various embodiments have been described in connection with the preferred embodiments of the various figures, it is to be understood that other similar embodiments may be used or modifications and additions may be made to the described embodiment for performing the same function without deviating therefrom. Therefore, the present invention should not be limited to any single embodiment, but rather should be construed in breadth and scope in accordance with the appended claims.

What is claimed is:

1. A catheter anchoring apparatus for securing a catheter assembly to a patient comprising:
    a first side member;
    a second side member;
    a crossmember connecting the second side member to the first side member, the first side member, the second side member and the crossmember generally extending in a first plane;
    a retaining assembly disposed on the crossmember and protruding from the first plane, the retaining assembly forming a channel having a central axis and being configured to removably receive a catheter hub of the catheter assembly;
    an adhesive on a bottom surface of the apparatus;
    a backing removably covering the adhesive;
    a first gripping tab on the first side member, the first gripping tab being formed by an upstanding wall extending from the first side member in a plane substantially perpendicularly to the first plane;
    a second gripping tab on the second side member, the second gripping tab being formed by an upstanding wall extending from the second side member in a plane substantially perpendicularly to the first plane;
    wherein a portion of at least one of the side members is scored to increase flexibility of the side member to facilitate flexing of a portion of the side member to deviate from the first plane.

2. The catheter anchoring apparatus of claim 1, wherein each of the side members includes a scored portion, the scored portions of the side members being oriented substantially parallel to each other.

3. The catheter anchoring apparatus of claim 1, wherein the scored portion of a said side member extends from one edge of the said side member to another edge of the said side member.

4. The apparatus of claim 1, wherein the first side member is elongated, the first side member having an upper portion, a lower portion, an inner side, and an outer side; and
  wherein the second side member is elongated, the second side member extending in a spaced, substantially parallel relation to the first side member, the second side member having a top portion, a bottom portion, an inner edge and an outer edge;
  wherein the catheter anchoring apparatus has a substantially H-shaped configuration, the crossmember having a top side, a bottom side, an outer first edge, an outer second edge, a front edge, and a rear edge;
  wherein the retaining assembly is located on the top side of the cross-member; and
  the backing having a size greater than a size of the bottom surface, a first portion of the backing covering the adhesive and a second portion being folded over the first portion, the second portion having a backing removal extension piece extending beyond a border of the bottom surface.

5. The catheter anchoring apparatus of claim 1, wherein the scored portion is formed by a substantially V-shaped groove in an upper surface of the said side member.

6. The catheter anchoring apparatus of claim 1, further comprising a support structure integrated with the retaining assembly, the support structure including a sloped element integrated into both sides of the retaining assembly, the sloped element extending between the retaining assembly and the cross-member.

7. The catheter anchoring apparatus of claim 1, wherein the scored portion of a said side member extends substantially linearly.

8. The catheter anchoring apparatus of claim 1, wherein the scored portion of a said side member extends substantially parallel to the central axis of the channel.

9. The catheter anchoring apparatus of claim 1, wherein the scored portion of the side member has a reduced thickness relative to an un-scored portion of the side member.

10. The catheter anchoring apparatus of claim 1, wherein a slit is formed through at least one of the gripping tabs, the slit being aligned with and extending from the scored portion of the at least one side member.

11. The catheter anchoring apparatus of claim 1, wherein a slit is formed through each of the gripping tabs, each slit being aligned with and extending from the scored portion of the respective side member.

12. The catheter anchoring apparatus of claim 1, wherein a slit is formed through one of the gripping tabs, the slit bisecting the gripping tab in a plane extending along the scored portion and being oriented substantially perpendicular to the first plane.

13. A catheter anchoring apparatus for securing a catheter assembly to a patient comprising:
  a first side member;
  a second side member;
  a crossmember connecting the second side member to the first side member such that the side members and crossmember form a substantially H-shaped configuration, the first side member, the second side member and the crossmember generally extending in a first plane;
  a retaining assembly disposed on the crossmember and protruding from the first plane, the retaining assembly forming a channel having a central axis and being configured to removably receive a catheter hub of the catheter assembly;
  an adhesive on a bottom surface of the apparatus;
  a backing removably covering the adhesive;
  a first gripping tab on the first side member, the first gripping tab being formed by an upstanding wall extending from the first side member in a plane substantially perpendicularly to the first plane;
  a second gripping tab on the second side member, the second gripping tab being formed by an upstanding wall extending from the second side member in a plane substantially perpendicularly to the first plane;
  wherein each of the side members is scored with a score line to increase flexibility of the respective side member to facilitate flexing of a portion of the side member to deviate from the first plane; and
  wherein a slit is formed through each of the gripping tabs, each slit being aligned with and extending from the scored portion of the respective side member.

14. The catheter anchoring apparatus of claim 13, wherein the score lines of the side members are oriented substantially parallel to each other.

15. The catheter anchoring apparatus of claim 13, wherein the score lines are oriented generally parallel to the central axis of the channel of the retaining assembly.

16. The catheter anchoring apparatus of claim 13, wherein the score line of a said side member extends from one edge of the said side member to another edge of the said side member.

17. The catheter anchoring apparatus of claim 13, wherein each score line is formed by a groove in an upper surface of the respective side member.

18. The catheter anchoring apparatus of claim 13, wherein the score line of a said side member extends substantially linearly.

19. The catheter anchoring apparatus of claim 13, wherein the score lines of the side members are oriented substantially parallel to each other;
  wherein the score lines are oriented generally parallel to the central axis of the channel of the retaining assembly;
  wherein the score line of a said side member extends from one edge of the said side member to another edge of the said side member;
  wherein each score line is formed by a groove in an upper surface of the respective side member; and
  wherein the score line of a said side member extends substantially linearly.

20. A catheter anchoring apparatus for securing a catheter assembly to a patient comprising:
  a first side member;
  a second side member;
  a crossmember connecting the second side member to the first side member, the first side member, the second side member and the crossmember generally extending in a first plane;
  a retaining assembly disposed on the crossmember and protruding from the first plane, the retaining assembly forming a channel having a central axis and being configured to removably receive a catheter hub of the catheter assembly;
  an adhesive on a bottom surface of the apparatus;
  a backing removably covering the adhesive;
  a first gripping tab on the first side member, the first gripping tab being formed by an upstanding wall extending from the first side member in a plane substantially perpendicularly to the first plane;

a second gripping tab on the second side member, the second gripping tab being formed by an upstanding wall extending from the second side member in a plane substantially perpendicularly to the first plane;

wherein a portion of each of the side members is scored with a groove to increase flexibility of the side member to facilitate flexing of a portion of the side member to deviate from the first plane; and wherein the gripping tabs extend in a tab plane, each of the grooves being oriented substantially perpendicular to the tab plane.

21. The catheter anchoring apparatus of claim 20, wherein the groove of one of the side members extends in a groove plane oriented perpendicular to the first plane, the gripping tab of the respective side member extending to and terminating at the groove plane.

22. The catheter anchoring apparatus of claim 1, wherein each of the side members includes a score line, the score lines of the side members being oriented substantially parallel to each other;

wherein the score line of a said side member extends from one edge of the said side member to another edge of the said side member;

wherein the first side member and the second side member are elongated, the second side member extending in a spaced, substantially parallel relation to the first side member such that the catheter anchoring apparatus has a substantially H-shaped configuration;

wherein the backing has a size greater than a size of the bottom surface of the apparatus, a first portion of the backing covering the adhesive and a second portion being folded over the first portion, the second portion having a backing removal extension piece extending beyond a border of the bottom surface;

wherein each score line is formed by a substantially V-shaped groove in an upper surface of a respective side member;

wherein the score line on a side member extends substantially linearly;

wherein the score line of a side member extends substantially parallel to the central axis of the channel;

wherein the score line of a side member has a reduced thickness relative to an un-scored portion of the side member;

wherein a slit is formed through each of the gripping tabs, each slit being aligned with and extending from the score line of the respective side member; and wherein the slits each bisect the respective gripping tab in a plane extending along the score line and being oriented substantially perpendicular to the first plane.

* * * * *